United States Patent
Miller

(10) Patent No.: US 9,439,667 B2
(45) Date of Patent: Sep. 13, 2016

(54) APPARATUS AND METHODS TO INSTALL, SUPPORT AND/OR MONITOR PERFORMANCE OF INTRAOSSEOUS DEVICES

(75) Inventor: Larry J. Miller, Spring Branch, TX (US)

(73) Assignee: Vidacare LLC, Wayne, PA (US)

( * ) Notice: Subject to any disclaimer, the term of this patent is extended or adjusted under 35 U.S.C. 154(b) by 89 days.

(21) Appl. No.: 12/947,312

(22) Filed: Nov. 16, 2010

(65) Prior Publication Data

US 2011/0098604 A1 Apr. 28, 2011

Related U.S. Application Data

(60) Division of application No. 11/461,885, filed on Aug. 2, 2006, now abandoned, which is a continuation-in-part of application No. 10/449,503, filed on May 30, 2003, now Pat. No. 7,670,328.

(60) Provisional application No. 60/384,756, filed on May 31, 2002.

(51) Int. Cl.
*A61B 5/103* (2006.01)
*A61M 5/00* (2006.01)
(Continued)

(52) U.S. Cl.
CPC ..... *A61B 17/32002* (2013.01); *A61B 17/3472* (2013.01); *A61B 17/3476* (2013.01); *A61M 5/158* (2013.01); *A61B 17/32053* (2013.01); *A61B 19/201* (2013.01); *A61B 2017/3492* (2013.01); *A61M 5/16836* (2013.01);
(Continued)

(58) Field of Classification Search
CPC ............ A61B 5/103; A61B 17/32002; A61B 17/3476; A61M 5/00
USPC ............ 173/216; 227/67, 131; 600/562–564; 604/21, 27, 135, 187; 606/80, 167, 606/170, 180
See application file for complete search history.

(56) References Cited

U.S. PATENT DOCUMENTS

| 1,539,637 A | 5/1925 | Bronner et al. |
| 2,317,648 A | 4/1943 | Siqveland et al. |

(Continued)

FOREIGN PATENT DOCUMENTS

| CA | 2454600 A1 | 2/2003 |
| DE | 10057931 A1 | 8/2002 |

(Continued)

OTHER PUBLICATIONS

"Proven reliability for quality bone marrow samples", Special Procedures, Cardinal Health, 6pages (2003).
(Continued)

*Primary Examiner* — Christopher Beccia
(74) *Attorney, Agent, or Firm* — Baker & Hostetler LLP

(57) ABSTRACT

Various types of supporting structures, supporting devices, attachment mechanisms and attachment techniques may be provided to support and/or stabilize an intraosseous device installed at a target site in a patient. Various methods and procedures may also be provided to releasably engage a supporting structure or supporting device proximate a target site. Apparatus and methods may be provided to monitor performance of an intraosseous device during communication of drugs, medications and/or fluids with an intraosseous space.

5 Claims, 5 Drawing Sheets

(51) Int. Cl.
  *A61B 17/32* (2006.01)
  *A61B 17/34* (2006.01)
  *A61M 5/158* (2006.01)
  *A61B 17/3205* (2006.01)
  *A61B 19/00* (2006.01)
  *A61M 5/168* (2006.01)

(52) U.S. Cl.
  CPC ............... *A61M2005/1581* (2013.01); *A61M 2005/1585* (2013.01); *A61M 2005/1588* (2013.01); *A61M 2210/08* (2013.01)

(56) References Cited

U.S. PATENT DOCUMENTS

| | | |
|---|---|---|
| 2,419,045 A | 4/1947 | Whittaker et al. |
| 2,773,501 A | 12/1956 | Young et al. |
| 3,104,448 A | 9/1963 | Morrow et al. |
| 3,120,845 A | 2/1964 | Horner et al. |
| 3,173,417 A | 3/1965 | Homer et al. |
| 3,175,554 A | 3/1965 | Stewart et al. |
| 3,507,276 A | 4/1970 | Burgess et al. |
| 3,529,580 A | 9/1970 | Stevens et al. |
| 3,543,966 A | 12/1970 | Ryan et al. |
| 3,815,605 A | 6/1974 | Schmidt et al. |
| 3,835,860 A | 9/1974 | Garretson |
| 3,893,445 A | 7/1975 | Hofsess |
| 3,991,765 A | 11/1976 | Cohen |
| 4,021,920 A | 5/1977 | Kirschner et al. |
| 4,099,518 A | 7/1978 | Baylis et al. |
| 4,124,026 A | 11/1978 | Berner et al. |
| 4,142,517 A | 3/1979 | Contreras et al. |
| 4,170,993 A | 10/1979 | Alvarez |
| 4,185,619 A | 1/1980 | Reiss |
| 4,194,505 A | 3/1980 | Schmitz |
| 4,213,462 A | 7/1980 | Sato |
| 4,258,722 A | 3/1981 | Sessions et al. |
| 4,262,676 A | 4/1981 | Jamshidi |
| 4,269,192 A | 5/1981 | Matsuo |
| 4,299,230 A | 11/1981 | Kubota |
| 4,306,570 A | 12/1981 | Matthews |
| 4,333,459 A | 6/1982 | Becker |
| 4,356,826 A | 11/1982 | Kubota |
| 4,381,777 A | 5/1983 | Garnier |
| 4,441,563 A | 4/1984 | Walton, II |
| 4,469,109 A | 9/1984 | Mehl |
| 4,484,577 A | 11/1984 | Sackner et al. |
| 4,543,966 A | 10/1985 | Islam et al. |
| 4,553,539 A | 11/1985 | Morris |
| 4,605,011 A | 8/1986 | Naslund |
| 4,620,539 A | 11/1986 | Andrews et al. |
| 4,623,335 A | 11/1986 | Jackson |
| 4,645,492 A | 2/1987 | Weeks |
| 4,646,731 A | 3/1987 | Brower |
| 4,654,492 A | 3/1987 | Koerner et al. |
| 4,655,226 A | 4/1987 | Lee |
| 4,659,329 A | 4/1987 | Annis |
| 4,692,073 A | 9/1987 | Martindell |
| 4,711,636 A | 12/1987 | Bierman |
| 4,713,061 A | 12/1987 | Tarello et al. |
| 4,716,901 A | 1/1988 | Jackson et al. |
| 4,723,945 A | 2/1988 | Theiling |
| 4,758,225 A | 7/1988 | Cox et al. |
| 4,762,118 A | 8/1988 | Lia et al. |
| 4,772,261 A | 9/1988 | Von Hoff et al. |
| 4,787,893 A | 11/1988 | Villette |
| 4,793,363 A | 12/1988 | Ausherman et al. |
| 4,801,293 A | 1/1989 | Jackson |
| 4,867,158 A | 9/1989 | Sugg |
| 4,919,146 A | 4/1990 | Rhinehart et al. |
| 4,919,653 A | 4/1990 | Martinez et al. |
| 4,921,013 A | 5/1990 | Spalink et al. |
| 4,935,010 A | 6/1990 | Cox et al. |
| 4,940,459 A | 7/1990 | Noce |
| 4,944,677 A | 7/1990 | Alexandre |
| 4,969,870 A | 11/1990 | Kramer et al. |
| 4,986,279 A | 1/1991 | O'Neill |
| 5,002,546 A | 3/1991 | Romano |
| 5,025,797 A | 6/1991 | Baran |
| 5,036,860 A | 8/1991 | Leigh et al. |
| 5,057,085 A | 10/1991 | Kopans |
| 5,074,311 A | 12/1991 | Hasson |
| 5,104,382 A | 4/1992 | Brinkerhoff et al. |
| 5,116,324 A | 5/1992 | Brierley et al. |
| 5,120,312 A | 6/1992 | Wigness et al. |
| 5,122,114 A | 6/1992 | Miller et al. |
| 5,133,359 A | 7/1992 | Kedem |
| 5,137,518 A | 8/1992 | Mersch |
| 5,139,500 A | 8/1992 | Schwartz |
| RE34,056 E | 9/1992 | Lindgren et al. |
| 5,172,701 A | 12/1992 | Leigh |
| 5,172,702 A | 12/1992 | Leigh et al. |
| 5,176,643 A | 1/1993 | Kramer et al. |
| 5,195,985 A | 3/1993 | Hall |
| 5,203,056 A | 4/1993 | Funk et al. |
| 5,204,670 A | 4/1993 | Stinton |
| 5,207,697 A | 5/1993 | Carusillo et al. |
| 5,209,721 A | 5/1993 | Wilk |
| 5,249,583 A | 10/1993 | Mallaby |
| 5,257,632 A | 11/1993 | Turkel et al. |
| 5,261,891 A | 11/1993 | Brinkerhoff et al. |
| 5,269,785 A | 12/1993 | Bonutti |
| 5,271,380 A | 12/1993 | Riek et al. |
| 5,271,744 A | 12/1993 | Kramer et al. |
| 5,279,306 A | 1/1994 | Mehl |
| 5,300,070 A | 4/1994 | Gentelia et al. |
| 5,312,361 A | 5/1994 | Zadini et al. |
| 5,312,364 A | 5/1994 | Jacobs |
| 5,315,737 A | 5/1994 | Ouimet |
| 5,324,300 A | 6/1994 | Elias et al. |
| 5,332,398 A | 7/1994 | Miller et al. |
| 5,333,790 A | 8/1994 | Christopher |
| 5,341,823 A | 8/1994 | Manosalva et al. |
| 5,344,420 A | 9/1994 | Hilal et al. |
| 5,348,022 A | 9/1994 | Leigh et al. |
| 5,357,974 A | 10/1994 | Baldridge |
| 5,368,046 A | 11/1994 | Scarfone et al. |
| 5,372,583 A | 12/1994 | Roberts et al. |
| 5,383,859 A | 1/1995 | Sewell, Jr. |
| 5,385,553 A | 1/1995 | Hart et al. |
| 5,389,553 A | 2/1995 | Grubisich et al. |
| 5,400,798 A | 3/1995 | Baran |
| 5,405,348 A | 4/1995 | Anspach, Jr. et al. |
| 5,405,362 A | 4/1995 | Kramer et al. |
| 5,421,821 A | 6/1995 | Janicki et al. |
| 5,423,796 A | 6/1995 | Shikhman et al. |
| 5,423,824 A | 6/1995 | Akerfeldt et al. |
| 5,431,151 A | 7/1995 | Riek et al. |
| 5,431,655 A | 7/1995 | Melker et al. |
| 5,432,459 A | 7/1995 | Thompson et al. |
| 5,436,566 A | 7/1995 | Thompson et al. |
| 5,451,210 A | 9/1995 | Kramer et al. |
| 5,454,791 A | 10/1995 | Tovey et al. |
| 5,480,388 A | 1/1996 | Zadini et al. |
| 5,484,442 A | 1/1996 | Melker et al. |
| D369,858 S | 5/1996 | Baker et al. |
| 5,526,820 A | 6/1996 | Khoury |
| 5,526,821 A | 6/1996 | Jamshidi |
| 5,527,290 A | 6/1996 | Zadini et al. |
| 5,529,580 A | 6/1996 | Kusunoki et al. |
| 5,549,565 A | 8/1996 | Ryan et al. |
| 5,554,154 A | 9/1996 | Rosenberg |
| 5,556,399 A | 9/1996 | Huebner |
| 5,558,737 A | 9/1996 | Brown et al. |
| 5,571,133 A | 11/1996 | Yoon |
| 5,586,847 A | 12/1996 | Mattern, Jr. et al. |
| 5,591,188 A | 1/1997 | Waisman |
| 5,595,186 A | 1/1997 | Rubinstein et al. |
| 5,599,347 A | 2/1997 | Hart et al. |
| 5,599,348 A | 2/1997 | Gentelia et al. |
| 5,601,559 A | 2/1997 | Melker et al. |
| 5,632,747 A | 5/1997 | Scarborough et al. |
| 5,685,820 A | 11/1997 | Riek et al. |
| 5,713,368 A | 2/1998 | Leigh |
| 5,724,873 A | 3/1998 | Hillinger |

(56) References Cited

U.S. PATENT DOCUMENTS

| | | |
|---|---|---|
| 5,733,262 A | 3/1998 | Paul |
| 5,752,923 A | 5/1998 | Terwilliger |
| 5,762,639 A | 6/1998 | Gibbs |
| 5,766,221 A | 6/1998 | Benderev et al. |
| 5,769,086 A | 6/1998 | Ritchart et al. |
| 5,779,708 A | 7/1998 | Wu |
| 5,800,389 A | 9/1998 | Burney et al. |
| 5,807,277 A | 9/1998 | Swaim |
| 5,810,826 A | 9/1998 | Lang.kerfeldt et al. |
| 5,817,052 A | 10/1998 | Johnson et al. |
| 5,823,970 A | 10/1998 | Terwilliger |
| D403,405 S | 12/1998 | Terwilliger |
| 5,858,005 A | 1/1999 | Kriesel |
| 5,865,711 A | 2/1999 | Chen |
| 5,868,711 A | 2/1999 | Kramer et al. |
| 5,868,750 A | 2/1999 | Schultz |
| 5,873,510 A | 2/1999 | Hirai et al. |
| 5,885,226 A | 3/1999 | Rubinstein et al. |
| 5,891,085 A | 4/1999 | Lilley et al. |
| 5,911,701 A | 6/1999 | Miller et al. |
| 5,911,708 A | 6/1999 | Teirstein |
| 5,916,229 A | 6/1999 | Evans |
| 5,919,172 A | 7/1999 | Golba, Jr. |
| 5,924,864 A | 7/1999 | Loge et al. |
| 5,927,976 A | 7/1999 | Wu |
| 5,928,238 A | 7/1999 | Scarborough et al. |
| 5,938,636 A * | 8/1999 | Kramer ............... A61M 5/1723 604/141 |
| 5,941,706 A | 8/1999 | Ura |
| 5,941,851 A | 8/1999 | Coffey et al. |
| 5,954,701 A | 9/1999 | Matalon |
| 5,960,797 A * | 10/1999 | Kramer ............... A61B 17/3472 128/898 |
| 5,980,545 A | 11/1999 | Pacala et al. |
| 5,984,919 A | 11/1999 | Hilal et al. |
| 5,993,417 A | 11/1999 | Yerfino et al. |
| 5,993,454 A | 11/1999 | Longo |
| 6,007,481 A | 12/1999 | Riek et al. |
| 6,007,496 A | 12/1999 | Brannon |
| 6,017,348 A | 1/2000 | Hart et al. |
| 6,018,094 A | 1/2000 | Fox |
| 6,022,324 A | 2/2000 | Skinner |
| 6,027,458 A | 2/2000 | Janssens |
| 6,033,369 A | 3/2000 | Goldenberg |
| 6,033,411 A | 3/2000 | Preissman |
| 6,063,037 A | 5/2000 | Mittermeier et al. |
| 6,071,284 A | 6/2000 | Fox |
| 6,080,115 A | 6/2000 | Rubinstein |
| 6,083,176 A | 7/2000 | Terwilliger |
| 6,086,543 A | 7/2000 | Anderson et al. |
| 6,086,544 A | 7/2000 | Hibner et al. |
| 6,096,042 A | 8/2000 | Herbert |
| 6,098,042 A | 8/2000 | Huynh |
| 6,102,915 A | 8/2000 | Bresler et al. |
| 6,106,484 A | 8/2000 | Terwilliger |
| 6,110,128 A | 8/2000 | Andelin et al. |
| 6,110,129 A | 8/2000 | Terwilliger |
| 6,110,174 A | 8/2000 | Nichter |
| 6,120,462 A | 9/2000 | Hibner et al. |
| 6,135,769 A | 10/2000 | Kwan |
| 6,159,163 A | 12/2000 | Strauss et al. |
| 6,183,442 B1 | 2/2001 | Athanasiou et al. |
| 6,210,376 B1 | 4/2001 | Grayson |
| 6,217,561 B1 | 4/2001 | Gibbs |
| 6,221,029 B1 | 4/2001 | Mathis et al. |
| 6,228,049 B1 | 5/2001 | Schroeder et al. |
| 6,228,088 B1 | 5/2001 | Miller et al. |
| 6,238,355 B1 | 5/2001 | Daum |
| 6,247,928 B1 | 6/2001 | Meller et al. |
| 6,248,110 B1 | 6/2001 | Reiley et al. |
| 6,257,351 B1 | 7/2001 | Ark et al. |
| 6,273,715 B1 | 8/2001 | Meller et al. |
| 6,273,862 B1 | 8/2001 | Privitera et al. |
| 6,283,925 B1 | 9/2001 | Terwilliger |
| 6,283,970 B1 | 9/2001 | Lubinus |
| 6,287,114 B1 | 9/2001 | Meller et al. |
| 6,302,852 B1 | 10/2001 | Fleming, III et al. |
| 6,309,358 B1 | 10/2001 | Okubo |
| 6,312,394 B1 | 11/2001 | Fleming, III |
| 6,315,737 B1 | 11/2001 | Skinner |
| 6,325,806 B1 | 12/2001 | Fox |
| 6,328,701 B1 | 12/2001 | Terwilliger |
| 6,328,744 B1 | 12/2001 | Harari et al. |
| 6,358,252 B1 | 3/2002 | Shapira |
| 6,402,701 B1 | 6/2002 | Kaplan et al. |
| 6,419,490 B1 | 7/2002 | Kitchings Weathers, Jr. |
| 6,425,888 B1 | 7/2002 | Embleton et al. |
| 6,428,487 B1 | 8/2002 | Burdorff et al. |
| 6,443,910 B1 | 9/2002 | Krueger et al. |
| 6,468,248 B1 | 10/2002 | Gibbs |
| 6,478,751 B1 | 11/2002 | Krueger et al. |
| 6,488,636 B2 | 12/2002 | Bryan et al. |
| 6,523,698 B1 | 2/2003 | Dennehey et al. |
| 6,527,736 B1 | 3/2003 | Attinger et al. |
| 6,527,778 B2 | 3/2003 | Athanasiou et al. |
| 6,540,694 B1 | 4/2003 | Van Bladel et al. |
| 6,547,511 B1 | 4/2003 | Adams |
| 6,547,561 B2 | 4/2003 | Meller et al. |
| 6,554,779 B2 | 4/2003 | Viola et al. |
| 6,555,212 B2 | 4/2003 | Boiocchi et al. |
| 6,582,399 B1 | 6/2003 | Smith et al. |
| 6,585,622 B1 | 7/2003 | Shum et al. |
| 6,595,911 B2 | 7/2003 | LoVuolo |
| 6,595,979 B1 | 7/2003 | Epstein et al. |
| 6,613,054 B2 | 9/2003 | Scribner et al. |
| 6,616,632 B2 | 9/2003 | Sharp et al. |
| 6,620,111 B2 | 9/2003 | Stephens et al. |
| 6,622,731 B2 | 9/2003 | Daniel et al. |
| 6,626,848 B2 | 9/2003 | Neuenfeldt |
| 6,626,887 B1 | 9/2003 | Wu |
| 6,638,235 B2 | 10/2003 | Miller et al. |
| 6,656,133 B2 | 12/2003 | Voegele et al. |
| 6,689,072 B2 | 2/2004 | Kaplan et al. |
| 6,690,308 B2 | 2/2004 | Hayami |
| 6,702,760 B2 | 3/2004 | Krause et al. |
| 6,702,761 B1 | 3/2004 | Damadian et al. |
| 6,706,016 B2 | 3/2004 | Cory et al. |
| 6,716,192 B1 | 4/2004 | Orosz, Jr. |
| 6,716,215 B1 | 4/2004 | David et al. |
| 6,716,216 B1 | 4/2004 | Boucher et al. |
| 6,730,043 B2 | 5/2004 | Krueger et al. |
| 6,730,044 B2 | 5/2004 | Stephens et al. |
| 6,749,576 B2 | 6/2004 | Bauer |
| 6,752,768 B2 | 6/2004 | Burdorff et al. |
| 6,752,816 B2 | 6/2004 | Culp et al. |
| 6,758,824 B1 | 7/2004 | Miller et al. |
| 6,761,726 B1 | 7/2004 | Findlay et al. |
| 6,770,070 B1 | 8/2004 | Balbierz |
| 6,796,957 B2 | 9/2004 | Carpenter et al. |
| 6,846,314 B2 | 1/2005 | Shapira |
| 6,849,051 B2 | 2/2005 | Sramek et al. |
| 6,855,148 B2 | 2/2005 | Foley et al. |
| 6,860,860 B2 | 3/2005 | Viola |
| 6,872,187 B1 | 3/2005 | Stark et al. |
| 6,875,163 B2 | 4/2005 | Cercone et al. |
| 6,875,183 B2 | 4/2005 | Cervi |
| 6,875,219 B2 | 4/2005 | Arramon et al. |
| 6,884,245 B2 | 4/2005 | Spranza, III |
| 6,887,209 B2 | 5/2005 | Kadziauskas et al. |
| 6,890,308 B2 | 5/2005 | Islam |
| 6,905,486 B2 | 6/2005 | Gibbs |
| 6,930,461 B2 | 8/2005 | Rutkowski |
| 6,942,669 B2 | 9/2005 | Kurc |
| 6,969,373 B2 | 11/2005 | Schwartz et al. |
| 7,008,381 B2 | 3/2006 | Janssens |
| 7,008,383 B1 | 3/2006 | Damadian et al. |
| 7,008,394 B2 | 3/2006 | Geise et al. |
| 7,025,732 B2 | 4/2006 | Thompson et al. |
| 7,063,672 B2 | 6/2006 | Schramm |
| 7,108,696 B2 | 9/2006 | Daniel et al. |
| 7,137,985 B2 | 11/2006 | Jahng |
| 7,182,752 B2 | 2/2007 | Stubbs et al. |
| 7,207,949 B2 | 4/2007 | Miles et al. |
| 7,226,450 B2 | 6/2007 | Athanasiou et al. |

(56) References Cited

U.S. PATENT DOCUMENTS

| | | |
|---|---|---|
| 7,229,401 B2 | 6/2007 | Kindlein |
| 7,285,112 B2 | 10/2007 | Stubbs et al. |
| 7,338,473 B2 | 3/2008 | Campbell et al. |
| 7,413,559 B2 | 8/2008 | Stubbs et al. |
| 7,670,328 B2 * | 3/2010 | Miller .................. 604/506 |
| 7,811,260 B2 | 10/2010 | Miller et al. |
| 7,850,620 B2 | 12/2010 | Miller et al. |
| 7,854,724 B2 | 12/2010 | Stearns et al. |
| 7,951,089 B2 | 5/2011 | Miller |
| 8,038,664 B2 | 10/2011 | Miller et al. |
| 8,088,189 B2 | 1/2012 | Matula et al. |
| 8,092,457 B2 | 1/2012 | Oettinger et al. |
| 8,142,365 B2 | 3/2012 | Miller |
| 8,216,189 B2 | 7/2012 | Stubbs et al. |
| 8,277,411 B2 | 10/2012 | Gellman |
| 8,282,565 B2 | 10/2012 | Mahapatra et al. |
| 8,317,815 B2 | 11/2012 | Mastri et al. |
| 8,419,683 B2 | 4/2013 | Miller et al. |
| 8,480,632 B2 | 7/2013 | Miller et al. |
| 8,668,698 B2 | 3/2014 | Miller et al. |
| 8,684,978 B2 | 4/2014 | Miller et al. |
| 8,715,219 B2 | 5/2014 | Stearns et al. |
| 8,715,287 B2 | 5/2014 | Miller |
| 8,814,807 B2 | 8/2014 | Hulvershorn et al. |
| 8,920,388 B2 | 12/2014 | Slocum et al. |
| 8,926,525 B2 | 1/2015 | Hulvershorn et al. |
| 8,961,451 B2 | 2/2015 | Stearns et al. |
| 8,974,569 B2 | 3/2015 | Matula et al. |
| 8,992,535 B2 | 3/2015 | Miller |
| 8,998,848 B2 | 4/2015 | Miller et al. |
| 9,067,030 B2 | 6/2015 | Stearns et al. |
| 9,072,543 B2 | 7/2015 | Miller et al. |
| 9,078,637 B2 | 7/2015 | Miller |
| 9,095,372 B2 | 8/2015 | Stearns et al. |
| 9,186,172 B2 | 11/2015 | Velez Rivera |
| 9,199,047 B2 | 12/2015 | Stearns et al. |
| 2001/0014439 A1 | 8/2001 | Meller et al. |
| 2001/0047183 A1 | 11/2001 | Privitera et al. |
| 2001/0053888 A1 | 12/2001 | Athanasiou et al. |
| 2002/0042581 A1 | 4/2002 | Cervi |
| 2002/0055713 A1 | 5/2002 | Gibbs |
| 2002/0120212 A1 | 8/2002 | Ritchart et al. |
| 2002/0133148 A1 * | 9/2002 | Daniel ............ A61B 18/1477 606/34 |
| 2002/0138021 A1 | 9/2002 | Pflueger |
| 2003/0028146 A1 | 2/2003 | Aves |
| 2003/0032939 A1 | 2/2003 | Gibbs |
| 2003/0036747 A1 | 2/2003 | Ie et al. |
| 2003/0050574 A1 | 3/2003 | Krueger |
| 2003/0114858 A1 | 6/2003 | Athanasiou et al. |
| 2003/0125639 A1 | 7/2003 | Fisher et al. |
| 2003/0153842 A1 | 8/2003 | Lamoureux et al. |
| 2003/0191414 A1 | 10/2003 | Reiley et al. |
| 2003/0195436 A1 | 10/2003 | Van Bladel et al. |
| 2003/0195524 A1 | 10/2003 | Barner |
| 2003/0199787 A1 | 10/2003 | Schwindt |
| 2003/0216667 A1 | 11/2003 | Viola |
| 2003/0225344 A1 | 12/2003 | Miller |
| 2003/0225364 A1 | 12/2003 | Kraft et al. |
| 2003/0225411 A1 | 12/2003 | Miller |
| 2004/0019297 A1 | 1/2004 | Angel |
| 2004/0019299 A1 | 1/2004 | Ritchart et al. |
| 2004/0034280 A1 | 2/2004 | Privitera et al. |
| 2004/0049128 A1 | 3/2004 | Miller et al. |
| 2004/0064136 A1 | 4/2004 | Papineau et al. |
| 2004/0073139 A1 | 4/2004 | Hirsch et al. |
| 2004/0092946 A1 | 5/2004 | Bagga et al. |
| 2004/0153003 A1 | 8/2004 | Cicenas et al. |
| 2004/0158172 A1 | 8/2004 | Hancock |
| 2004/0158173 A1 | 8/2004 | Voegele et al. |
| 2004/0162505 A1 | 8/2004 | Kaplan et al. |
| 2004/0191897 A1 | 9/2004 | Muschler |
| 2004/0210161 A1 | 10/2004 | Burdorff et al. |
| 2004/0215102 A1 | 10/2004 | Ikehara et al. |
| 2004/0220497 A1 | 11/2004 | Findlay et al. |
| 2005/0027210 A1 | 2/2005 | Miller |
| 2005/0040060 A1 | 2/2005 | Andersen et al. |
| 2005/0075581 A1 | 4/2005 | Schwindt |
| 2005/0085838 A1 | 4/2005 | Thompson et al. |
| 2005/0101880 A1 | 5/2005 | Cicenas et al. |
| 2005/0113716 A1 | 5/2005 | Mueller et al. |
| 2005/0124915 A1 | 6/2005 | Eggers et al. |
| 2005/0131345 A1 | 6/2005 | Miller |
| 2005/0148940 A1 | 7/2005 | Miller |
| 2005/0165328 A1 | 7/2005 | Heske et al. |
| 2005/0165403 A1 | 7/2005 | Miller |
| 2005/0165404 A1 | 7/2005 | Miller |
| 2005/0171504 A1 | 8/2005 | Miller |
| 2005/0182394 A1 | 8/2005 | Spero et al. |
| 2005/0200087 A1 | 9/2005 | Vasudeva et al. |
| 2005/0203439 A1 | 9/2005 | Heske et al. |
| 2005/0209530 A1 | 9/2005 | Pflueger |
| 2005/0215921 A1 | 9/2005 | Hibner et al. |
| 2005/0228309 A1 | 10/2005 | Fisher et al. |
| 2005/0261693 A1 | 11/2005 | Miller et al. |
| 2006/0011506 A1 | 1/2006 | Riley |
| 2006/0036212 A1 | 2/2006 | Miller |
| 2006/0052790 A1 | 3/2006 | Miller |
| 2006/0074345 A1 | 4/2006 | Hibner |
| 2006/0079774 A1 | 4/2006 | Anderson |
| 2006/0089565 A1 | 4/2006 | Schramm |
| 2006/0115066 A1 | 6/2006 | Levien et al. |
| 2006/0122535 A1 | 6/2006 | Daum |
| 2006/0129082 A1 | 6/2006 | Rozga |
| 2006/0144548 A1 | 7/2006 | Beckman et al. |
| 2006/0149163 A1 | 7/2006 | Hibner et al. |
| 2006/0167377 A1 | 7/2006 | Ritchart et al. |
| 2006/0167378 A1 | 7/2006 | Miller |
| 2006/0167379 A1 | 7/2006 | Miller |
| 2006/0173480 A1 | 8/2006 | Zhang |
| 2006/0184063 A1 | 8/2006 | Miller |
| 2006/0189940 A1 | 8/2006 | Kirsch |
| 2007/0016100 A1 | 1/2007 | Miller |
| 2007/0049945 A1 | 3/2007 | Miller |
| 2007/0149920 A1 | 6/2007 | Michels et al. |
| 2007/0213735 A1 | 9/2007 | Saadat et al. |
| 2007/0270712 A1 | 11/2007 | Wiksell et al. |
| 2007/0270775 A1 | 11/2007 | Miller et al. |
| 2008/0015467 A1 | 1/2008 | Miller |
| 2008/0015468 A1 | 1/2008 | Miller |
| 2008/0045857 A1 | 2/2008 | Miller et al. |
| 2008/0045860 A1 | 2/2008 | Miller et al. |
| 2008/0045861 A1 | 2/2008 | Miller et al. |
| 2008/0045965 A1 | 2/2008 | Miller et al. |
| 2008/0140014 A1 | 6/2008 | Miller et al. |
| 2008/0215056 A1 | 9/2008 | Miller et al. |
| 2008/0221580 A1 | 9/2008 | Miller et al. |
| 2009/0131832 A1 | 5/2009 | Sacristan et al. |
| 2010/0137740 A1 | 6/2010 | Miller |
| 2011/0046477 A1 | 2/2011 | Hulvershorn et al. |
| 2011/0082387 A1 | 4/2011 | Miller et al. |
| 2011/0098604 A1 | 4/2011 | Miller |
| 2011/0125084 A1 | 5/2011 | Stearns et al. |
| 2011/0288405 A1 | 11/2011 | Razavi et al. |
| 2012/0109061 A1 | 5/2012 | Miller et al. |
| 2012/0150101 A1 | 6/2012 | Stearns et al. |
| 2012/0283582 A1 | 11/2012 | Mahapatra et al. |
| 2012/0323071 A1 | 12/2012 | Gellman |
| 2012/0330184 A1 | 12/2012 | Mahapatra et al. |
| 2014/0005657 A1 | 1/2014 | Brannan et al. |
| 2014/0188038 A1 | 7/2014 | Stearns et al. |
| 2014/0336567 A1 | 11/2014 | Stearns et al. |
| 2014/0343454 A1 | 11/2014 | Miller et al. |
| 2014/0358070 A1 | 12/2014 | Stearns et al. |
| 2015/0025363 A1 | 1/2015 | Hulvershorn et al. |
| 2015/0057530 A1 | 2/2015 | Roggeveen et al. |
| 2015/0112261 A1 | 4/2015 | Bassett et al. |
| 2015/0173818 A1 | 6/2015 | Baroud et al. |
| 2015/0202390 A1 | 7/2015 | Stearns et al. |
| 2015/0202391 A1 | 7/2015 | Stearns et al. |
| 2015/0342635 A1 | 12/2015 | Tsamir et al. |
| 2015/0366569 A1 | 12/2015 | Miller |

(56) References Cited

U.S. PATENT DOCUMENTS

FOREIGN PATENT DOCUMENTS

| | | |
|---|---|---|
| EP | 0517000 A2 | 12/1992 |
| EP | 0807412 A1 | 11/1997 |
| EP | 1314452 A1 | 5/2003 |
| FR | 2457105 A1 | 12/1980 |
| FR | 2516386 A1 | 5/1983 |
| FR | 2931451 A1 | 11/2009 |
| GB | 2130890 A | 6/1984 |
| JP | H1052433 A | 2/1998 |
| WO | 9307819 A2 | 4/1993 |
| WO | 9631164 A1 | 10/1996 |
| WO | 9806337 A1 | 2/1998 |
| WO | 9918866 A1 | 4/1999 |
| WO | 9952444 A1 | 10/1999 |
| WO | 0056220 A1 | 9/2000 |
| WO | 0178590 A1 | 10/2001 |
| WO | 0241792 A1 | 5/2002 |
| WO | 2005110259 A1 | 11/2005 |
| WO | 2005112800 A2 | 12/2005 |
| WO | 2008081438 A1 | 7/2008 |

OTHER PUBLICATIONS

Astrom, K. Gunnar 0., "CT-guided Transsternal Core Biopsy of Anterior Mediastinal Masses," Radiology 1996; 199:564-567 (May 1996).
Astrom, K.G., "Automatic Biopsy Instruments Used Through a Coaxial Bone Biopsy System with an Eccentric Drill Tip," Acta Radiological, 1995; 36:237-242 (May 1995).
Australian Exam Report on Patent Application no. 2003240970, 2 pages (Oct. 15, 2007).
BioAccess.com, Single Use Small Bone Power Tool—How It Works, 1 pg (Jun. 9, 2008).
Buckley et al., CT-guided bone biopsy: Initial experience with commercially available handheld Black and Decker drill, European Journal of Radiology 61 pp. 176-180 (2007).
Chinese Office Action, Application No. 2005800003261, (with English translation), 9 pgs. (Jan. 16, 2009).
Chinese Office Action, Application No. 200780000590.6, (with English translation), 13 pgs. (Aug. 21, 2009).
Communication Pursuant to Article 94(3) EPC, Application No. 05 712 091.7-1265, 4 pages (Apr. 8, 2008).
Communication relating to the results of the partial International Search Report forPCT/US2005/002484, 6 pages (May 19, 2005).
Cummins, Richard, et al, "ACLS-Principles and Practice", ACLS-The Reference rexlbook, American Heart Association on. 214-218 (2003).
European Office Action and Search Report, Application No. 09150973.7, 8 pages (Oct. 23, 2009).
European Office Action Communication, Application No. 08158699.2-1265/1967142, 10 pages (Nov. 4, 2008).
European Office Action EP03731475.4, 4 pages (Oct. 11, 2007).
European Search Report 08158699.2-1265, 4 pages (Aug. 2008).
F.A.S.T. 1 Intraosseous Infusion System with Depth-Control Mechanism Brochure, 6 pages (2000).
Gunal et al., Compartment Syndrome After Intraosseous Infusion: An Experimental Study in Dogs, Journal of Pediatric Surgery, vol. 31, No. 11, pp. 1491-1493 (Nov. 1996).
Hakan et al., CT-guided Bone Biopsy Performed by Means of Coaxial Biopsy System with anEccentric Drill, Radiology, pp. 549-552 (Aug. 93).
International PCT Search Report and Written Opinion PCT/US2004/037753, 16 pages (Jul. 8, 2005).
International PCT Search Report and Written Opinion PCT/US2005/002484, 15 pages (Jul. 22, 2005).
International PCT Search Report PCT/US03/17167, 8 pages (Sep. 16, 2003).
International PCT Search Report PCT/US03117203, 8 pages (Sep. 16, 2003).
International PCT Search Report PCT/US2004/037753, 6 pages (Apr. 9, 2005).
International Preliminary Report on Patentability PCT/US2005/002484, 9 pages (Aug. 3, 2006).
International Preliminary Report on Patentability, PCT/US/2007/072209, 10 pages (May 14, 2009).
International Preliminary Report on Patentability, PCT/US/2007/078203, 13 pages (Mar. 26, 2009).
International Preliminary Report on Patentability, PCT/US/2007/078204, 11 pages (Apr. 2, 2009).
International Preliminary Report on Patentability, PCT/US/2007/078205, 10 pages (Mar. 26, 2009).
International Preliminary Report on Patentability, PCT/US/2007/078207, 10 pages (Mar. 26, 2009).
International Preliminary Report on Patentability, PCT/US08/52943, 7 pages (Oct. 15, 2009).
International Preliminary Report on Patentability, PCT/US2007/072202, 10 pages (Jan. 15, 2009).
International Preliminary Report on Patentability, PCT/US2007/072217, 11 pages (Feb. 12, 2009).
International Preliminary Report, PCT/US2005/002484, 9 pages (Aug. 3, 2006).
International Search Report and Written Opinion for International Application No. PCT/US2006/025201, 18 pages (Jan. 29, 2007).
International Search Report and Written Opinion, PCT/US08/500346, 12 pages (May 22, 2008).
International Search Report and Written Opinion, PCT/US08/52943, 8 pages (Sep. 26, 2008).
International Search Report and Written Opinion, PCT/US2007/072202, 17 pages (Mar. 25, 2008).
International Search Report and Written Opinion, PCT/US2007/078203, 15 pages (May 13, 2008).
International Search Report and Written Opinion, PCT/US2007/078204, 14 pages (May 15, 2008).
International Search Report and Written Opinion, PCT/US2007/078205, 13 pages (Sep. 11, 2007).
International Search Report and Written Opinion, PCT/US2007/078207, 13 pages (Apr. 7, 2008).
International Search Report and Written Opinion, PCT/USOB/500346, 12 pages (May 22, 2008).
International Search Report, PCT/US2006/025201, 12 pages (Feb. 7, 2008).
International Search Report, PCT/US2007/072209, 18 pages (Apr. 25, 2008).
International Search Report, PCT/US2007/072209, 9 pages (Mar. 12, 2007).
International Search Report, PCT/US2007/072217, 20 pages (Mar. 31, 2008).
International Search Report, PCT/US2007/072217, 9 pages (Mar. 12, 2007).
Japanese Office Action, Application No. 2004-508,669, (with English summary), 9 pgs. (Aug. 3, 2009).
Japanese Office Action, Application No. 2004-508,670, (with English summary), 13 pgs. (Apr. 21, 2009).
Liakat A. Parapia, Trepanning or trephines: a history of bone marrow biopsy, British Journalof Haematology, pp. 14-19 (2007).
International PCT Search Report PCT/US2004/037753, 6 pages (Apr. 19, 2005).
Michael Trotty, "Technology (A Special Report)—The Wall Street Journal 2008 Technology Innovation Awards—This years winners include: an IV alternative, a better way to make solar panels, a cheap, fuel efficient car and a better way to see in the dark", The Wall StreetJournal, Factiva, 5 pages (2008).
Official Action for European Application No. 03756317.8, 4 pages (Dec. 28, 2006).
PCT Invitation to Pay Additional Fees, PCT/US2007/072209, 9 pages (Dec. 3, 2007).
PCT Preliminary Report on Patentability, PCT/US/2008/050346, 8 pgs. (Jul. 23, 2009).

(56) References Cited

OTHER PUBLICATIONS

Pediatric Emergency, Intraosseous Infusion for Administration of Fluids and Drugs, www.cookgroup.com, 1 pg (2000).

Pediatrics, "2005 American Heart Association Guidelines for Cardiopulmonary Resuscitation and Emergency Cardiovascular Care of Pediatric and Neonatal Patients: Pediatric Advanced Life Support," www.pediatrics.org, Official Journal of the American Academy of Pediatrics, 26 pages (Feb. 21, 2007).

Richard Cummins et al, "ACLS-Principles and Practice", ACLS-The Reference Textbook, American Heart Association, pp. 214-218 (2003).

Riley et al., A Pathologists Perspective on Bone Marrow Aspiration Biopsy: I. Perle rmlng a Bone Marrow Examination• Journal of Clinical Laboratory Anatylsis, 18 pp. 70-90 (2004).

Vidacare Corporation Comments to Intraosseous Vascular Access Position Paper, Infusion Nurses Society, 6 pages (May 4, 2009).

* cited by examiner

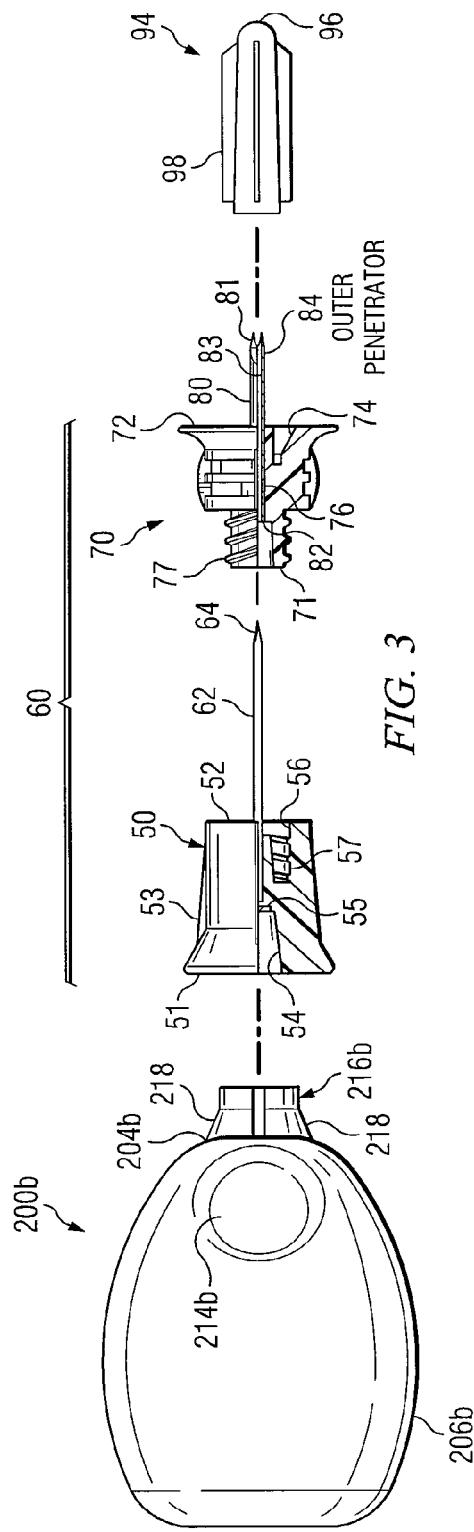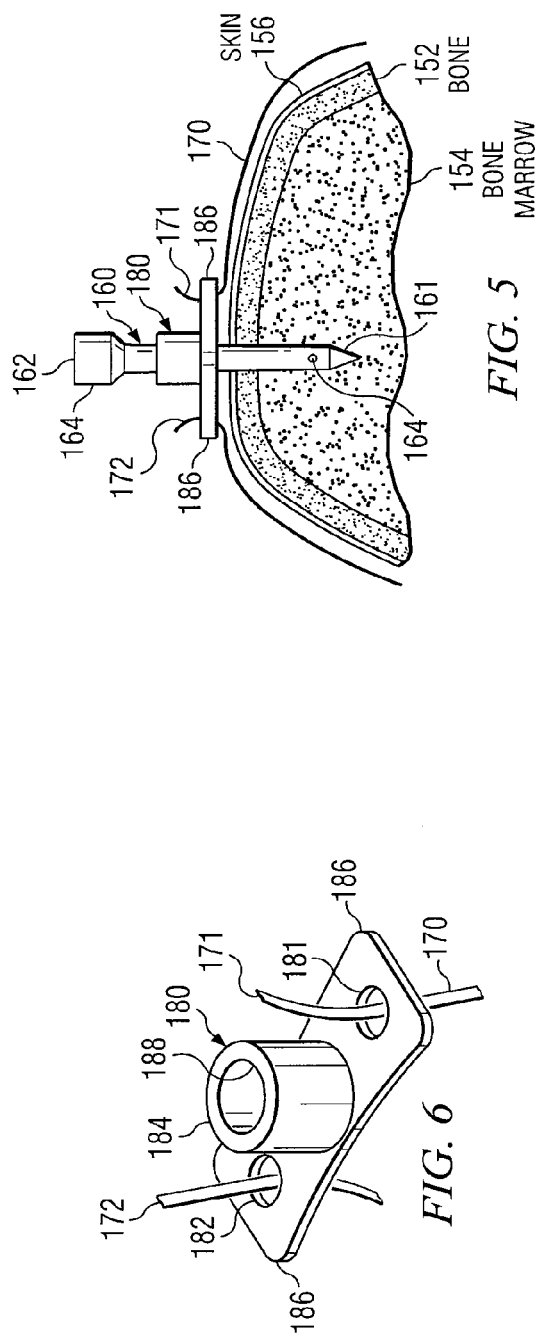

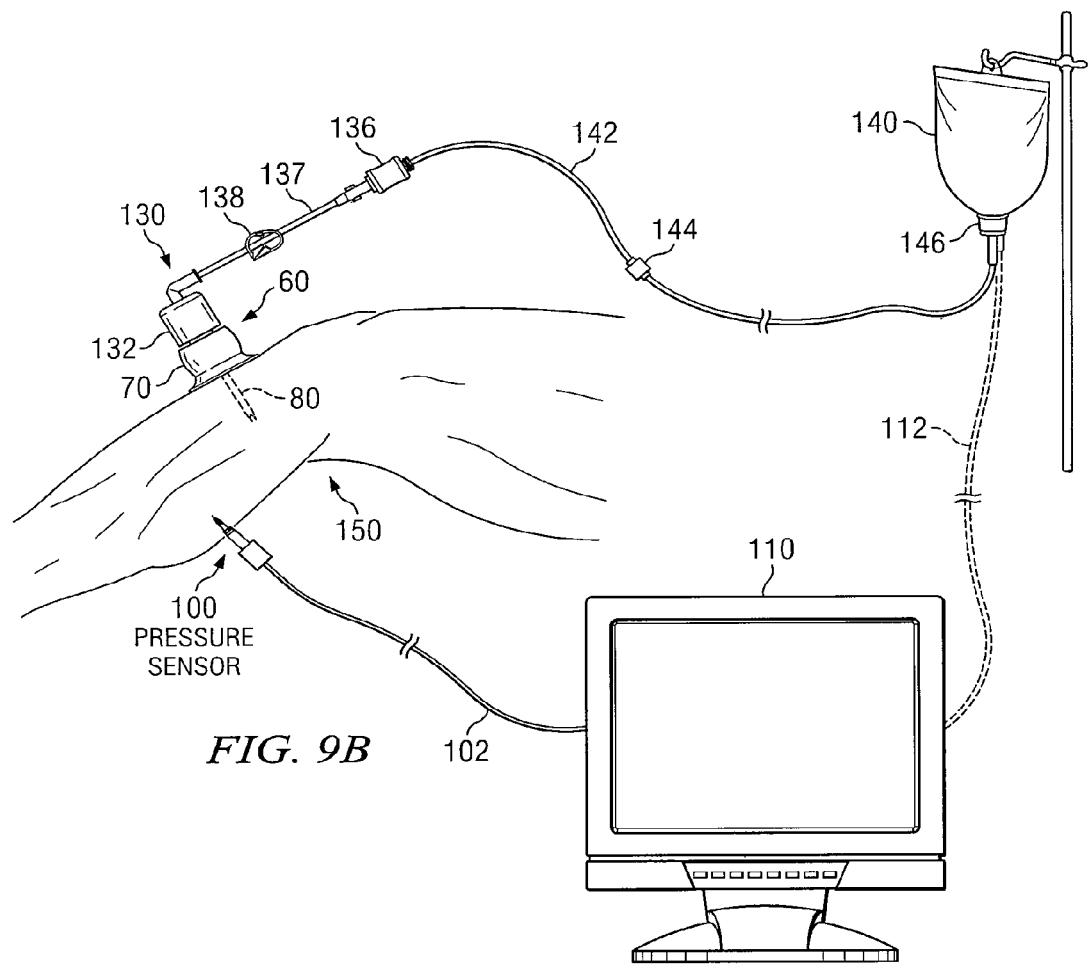
FIG. 9B
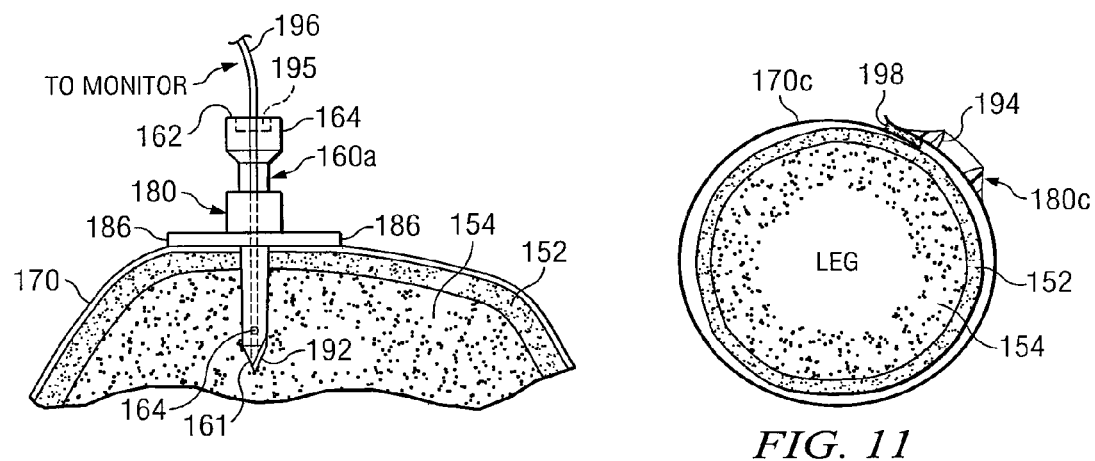
FIG. 10
FIG. 11

APPARATUS AND METHODS TO INSTALL, SUPPORT AND/OR MONITOR PERFORMANCE OF INTRAOSSEOUS DEVICES

RELATED APPLICATIONS

This application is a Divisional application of U.S. patent application Ser. No. 11/461,885 filed Aug. 2, 2006 now abandoned, which is a Continuation-In-Part application of U.S. patent application Ser. No. 10/449,503 filed May 30, 2003 now U.S. Pat. No. 7,670,328, which claims the benefit of U.S. Provisional Patent Application Ser. No. 60/384,756, filed May 31, 2002. The contents of these applications are incorporated herein in their entirety by this reference.

TECHNICAL FIELD

The present disclosure is related to apparatus and methods which may be used to support an intraosseous device after insertion into a target site and/or to monitor performance of the intraosseous device while communicating fluid with bone marrow and/or other soft body tissue.

BACKGROUND OF THE DISCLOSURE

Vascular access is often essential to viability of a patient in emergency situations, during transportation to a medical facility and during treatment at the medical facility. Obtaining vascular access may be a significant problem in five to ten percent of patients of all ages and weight in pre-hospital and hospital environments. This equates to approximately six (6) million patients in the U.S. annually. For example patients suffering from conditions such as shock, cardiac arrest, drug overdose, dehydration, diabetic coma, renal failure and altered states of consciousness may have very few (if any) accessible veins.

In a hospital or similar medical facility, central line access is often an alternative to IV access. However, central line access generally takes longer, costs more, may have a higher risk of complications and requires skilled personnel to properly insert the central line. In many hospital environments, nurses and physicians are increasingly turning to intraosseous (IO) access as an alternative to IV access, rather than central lines. In pre-hospital environments, paramedics and other emergency medical service (EMS) providers are often finding that IO access may be quick, safe and effective when IV placement is challenging.

The intraosseous space typically functions as a non-collapsible vein available for infusion of drugs, blood and other fluids that reach a patient's central circulation within seconds and frequently with minimal patient discomfort. Current guidelines indicate that IO access may become the standard of care for many cardiac arrest patients further indicating that IO access is similar to central line access in efficacy and may carry less risk of complications for both patients and EMS providers.

SUMMARY OF THE DISCLOSURE

In accordance with teachings of the present disclosure, apparatus and methods are provided to facilitate access to a patient's vascular system and to monitor results of such access as appropriate. Intraosseous (IO) devices incorporating teachings of the present disclosure may be installed at selected insertion sites or target areas to infuse drugs and communicate various fluids with a patient's bone marrow. Supporting structures and attachment techniques incorporating teachings of the present disclosure may be used to enhance performance of various types of IO devices.

One aspect of the present disclosure may include providing apparatus and methods for stabilizing or securing an intraosseous device disposed in bone marrow or other soft tissue. Supporting structures, attachment devices and attachment techniques incorporating teachings of the present disclosure may be used with a wide variety of intraosseous devices.

Another aspect of the present disclosure may include the use of one or more sensors to monitor performance of an intraosseous device during infusion of drugs and/or communication of fluids with a patient's vascular system.

The present disclosure may provide apparatus and methods to establish vascular access during treatment at a wide variety of locations and facilities including, but not limited to, accident sites, emergency rooms, battlefields, emergency medical services (EMS) facilities, oncology treatment centers, chronic disease treatment facilities and veterinary applications.

BRIEF DESCRIPTION OF THE DRAWINGS

A more complete and thorough understanding of the present embodiments and advantages thereof may be acquired by referring to the following description taken in conjunction with the accompanying drawings, in which like reference numbers indicate like features, and wherein:

FIG. 3 is a schematic drawing in section and in elevation with portions broken away showing an exploded view of a manual driver and associated intraosseous device;

FIG. 5 is a schematic drawing in section with portions showing an intraosseous device inserted into a bone and associated bone marrow along with a supporting structure and attachment mechanism incorporating teachings of the present disclosure;

FIG. 6 is a schematic drawing showing an isometric view with portions broken away of the supporting structure and attachment mechanism in FIG. 5;

FIG. 9B is a schematic drawing in section and in elevation with portions broken away showing an intraosseous device inserted into bone marrow of a patient and a pressure monitoring device inserted into an adjacent compartment and monitoring equipment incorporating teachings of the present disclosure;

FIG. 10 is a schematic drawing in section with portions broken away showing an intraosseous device inserted into bone and associated bone marrow along with another example of a supporting structure, attachment mechanism and monitoring device incorporating teachings of the present disclosure;

FIG. 11 is a schematic drawing in section showing another example of a supporting structure and attachment mechanism incorporating teachings of the present disclosure releasably engaged with a patient's leg;

DETAILED DESCRIPTION OF THE DISCLOSURE

Figure 1:
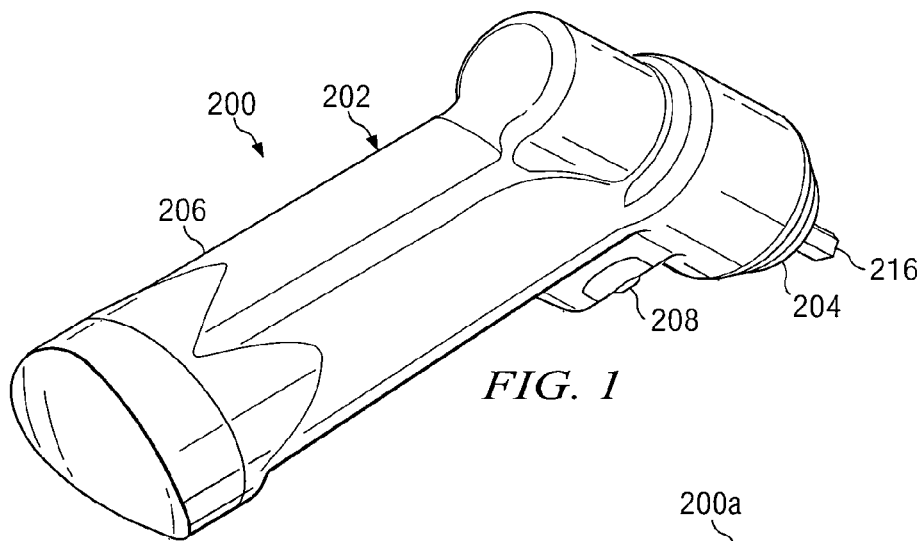
FIG. 1 is a schematic drawing showing an isometric view of a powered driver which may be used to insert an intraosseous device at a selected site in a patient.

Preferred embodiments of the disclosure and its advantages are best understood by reference to FIGS. 1-15B wherein like numbers refer to same and like parts.

Vascular system access may be essential for treatment of many serious diseases, chronic conditions and acute emergency situations. Yet, many patients experience extreme difficulty obtaining effective treatment because of inability to obtain or maintain intravenous (IV) access. An intraosseous (IO) space provides a direct conduit to a patent's vascular system and systemic circulation. Therefore, IO access is an effective route to administer a wide variety of drugs, other medications and fluids. Rapid IO access offers great promise for almost any serious emergency that requires vascular access to administer life saving drugs, other medications and/or fluids when traditional IV access is difficult or impossible.

The upper tibia proximate a patient's knee may often be used as an insertion site for an IO device to establish access with a patient's vascular system. The humerus in a patient's arm may also be used as an insertion site for IO access to a patient's vascular system. However, teachings of the present disclosure are not limited to treatment of human patients. Various teachings of the present disclosure may also be used during treatment of animals in a veterinary practice IO access may be used as a "bridge" (temporary fluid and drug therapy) during emergency conditions until conventional IV sites can be found and utilized. This often occurs because fluids and/or medication provided via an IO access may stabilize a patient and expand veins and other portions of a patient's vascular system. IO devices and associated procedures incorporating teachings of the present disclosure may become the standard of care for administering medications and fluids in situations when IV access is difficult or not possible.

Intraosseous access may be used as a "routine" procedure with chronic conditions which substantially reduce or eliminate the availability of conventional IV sites. Examples of such chronic conditions may include, but are not limited to, dialysis patients, seriously ill patients in intensive care units and epilepsy patients. Intraosseous devices along with supporting structure and/or monitoring equipment incorporating teachings of the present disclosure may be quickly and safely used to provide IO access to a patient's vascular system in difficult cases such as status epilepticus to give medical personnel an opportunity to administer crucial medications and/or fluids. Further examples of such acute and chronic conditions are listed near the end of this written description.

The ability to satisfactorily insert an intraosseous (IO) device such as an IO needle at a desired insertion site may be problematic when a patient is moving or has the potential to move. Inserting an IO device in the wrong place may expose a patient to potential harm. Patient movement may be of special concern for patients suffering from status epilepticus or violent patients (drug overdoses or mental status changes) that need to be controlled for their safety and treatment. Epileptic patients may shake violently for prolonged periods which makes starting a conventional IV nearly impossible. Likewise, it may be difficult to accurately place an IO device at a desired insertion site in such patients.

Although target areas or insertion sites for successful IO placement such as a patient's tibia and humerus are often larger than target areas for placement of an IV device, problems with inserting an IO device may be minimized by using supporting structures along with attachment mechanisms and attachment techniques incorporating teachings of the present disclosure. Such supporting structures, attachment mechanisms and attachment techniques may be easy to apply, even in difficult field environments.

The term "driver" may be used in this application to include any type of powered driver or manual driver satisfactory for inserting an intraosseous (IO) device such as a penetrator assembly or an IO needle into selected portions of a patient's vascular system. Various techniques may be satisfactorily used to releasably engage or attach an IO device and/or penetrator assembly with manual drivers and powered drivers. For some applications a powered driver or a manual driver may be directly coupled with an IO device. For other applications various types of connectors may be used to couple a manual driver or a powered driver with an IO device. A wide variety of connectors and associated connector receptacles, fittings and/or other types of connections with various dimensions and configurations may be satisfactorily used to releasably engage an IO device with a powered driver or a manual driver.

The term "intraosseous (IO) device" may be used in this application to include any hollow needle, hollow drill bit, penetrator assembly, bone penetrator, cannula, trocar, inner penetrator, outer penetrator, IO needle or IO needle set operable to provide access to an intraosseous space or interior portions of a bone. A wide variety of trocars, spindles and/or shafts may be disposed within a cannula during installation at a selected target site. Such trocars, spindles and shafts may also be characterized as inner penetrators. A cannula may be characterized as an outer penetrator.

The term "fluid" may be used within this patent application to include any liquid including, but not limited to, blood, water, saline solutions, IV solutions, plasma or any mixture of liquids, particulate matter, dissolved medication and/or drugs appropriate for injection into bone marrow or other target sites. The term "fluid" may also be used within this patent application to include body fluids such as, but not limited to, blood and cells which may be withdrawn from a target site.

Various features of the present disclosure may be described with respect to powered driver 200 and/or manual drivers 200a and 200b. Various features of the present disclosure may also be described with respect to intraosseous devices 60, 160 and 160a. However, supporting structures, attachment mechanisms and attachment techniques incorporating teachings of the present disclosure may be satisfactorily used with a wide variety of drivers and intraosseous devices. The present disclosure is not limited to use with intraosseous devices 60, 160 or 160a or drivers 200, 200a or 200b.

Powered driver 200 may include housing 202 with various types of motors and/or gear assemblies disposed therein (not expressly shown). A rotatable shaft (not expressly shown) may be disposed within housing 202 and connected with a gear assembly (not expressly shown). Various types of fittings, connections, connectors and/or connector receptacles may be provided at one end of the rotatable shaft extending from end 204 of housing 202.

For some applications pin type fitting or connector 216 may be formed on the one end of the rotatable shaft. A matching box type fitting or connector receptacle may be provided on an intraosseous device so that connector 216 of powered driver 200 may be releasably engaged with the intraosseous device. For some applications, connector 216 may have a pentagonal shaped cross section with tapered surfaces formed on the exterior thereof.

Handle 206 may include a battery (not expressly shown) or other power source. Handle 206 may also include trigger assembly 208 for use in activating powered driver 200. Examples of powered drivers are shown in pending patent applications Ser. No. 10/449,503 filed May 30, 2003 entitled "Apparatus and Method to Provide Emergency Access To Bone Marrow," now U.S. Pat. No. 7,670,328; Ser. No. 10/449,476 filed May 30, 2003 entitled "Apparatus and Method to Access Bone Marrow," now U.S. Pat. No. 7,699,850; and Ser. No. 11/042,912 filed Jan. 25, 2005 entitled "Manual Intraosseous Device," now U.S. Pat. No. 8,641,715.

Figure 2:
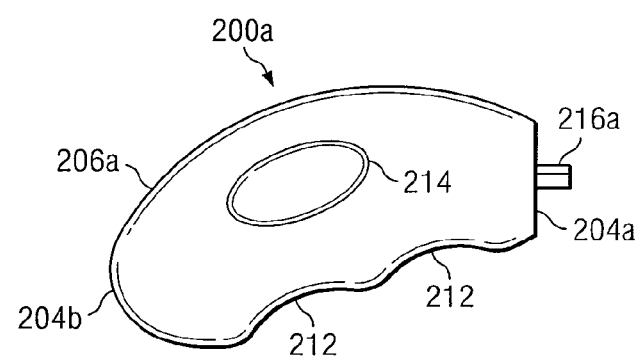
FIG. 2 is a schematic drawing showing a side view of a manual driver which may be used to insert an intraosseous device at a selected target area for a patient.

FIG. 2 shows one example of a manual driver which may be satisfactorily used to insert an intraosseous device into a selected target area. For this embodiment manual driver 200a may be generally described as having handle 206a with a "pistol grip" configuration. Handle 206a have an ergonomical design with finger grips 212 and one or more finger rests 214.

Connector 216a may extend from first end 204a of handle 206a. Connector 216a may have a configuration and dimensions similar to previously described connector 216. However, manual drivers may be provided with a wide variety of connectors and/or connector receptacles.

FIG. 3 is a schematic drawing showing an exploded view of a manual driver and a penetrator assembly which may be used to provide access to a patient's vascular system. For embodiments such as shown in FIG. 3, manual driver 200b may be described as having a generally bulbous or oval shaped handle 206b with one or more finger rests 214b disposed on the exterior thereof. Connector 216b may extend from end 204b of manual driver 200b for releasable engagement with IO device or penetrator assembly 60.

Connector 216b may include multiple segments or wedges sized to be received within corresponding portions of a connector receptacle. A drive shaft (not expressly shown) may also be disposed within wedges 218. Various details concerning this type of connector and connector receptacle are discussed in more detail in pending U.S. patent application Ser. No. 11/042,912 filed Jan. 12, 2005, entitled "Manual Intraosseous Driver," now U.S. Pat. No. 8,641,715.

Penetrator assembly or IO device 60 may include connector 50 and hub 70. Connector 50 may be described as having a generally cylindrical configuration defined in part by first end 51 and second end 52. First end 51 may have a connector receptacle disposed therein and sized to receive connectors 216, 216a and/or 216b.

First end 51 may include opening 54 formed with various configurations and/or dimensions. For some applications opening 54 may be sized to receive portions of a drive shaft. One or more webs (not expressly shown) may be formed in end 51 extending from opening 54. Open segments or void spaces (not expressly shown) may be formed between such webs. Respective segments 218 extending from adjacent portions of handle 200b may be releasably engaged with such webs and void spaces. Opening 54 and associated webs may be used to releasably engage connector 50 with either a manual driver or a powered driver.

The configuration and dimensions of opening 54 may be selected to be compatible with releasably engaging connector 50 of penetrator assembly 60 with connector 216b extending of manual driver 200b. For some applications metallic disk 55 may be disposed within opening 54 for use in releasably engaging penetrator assembly 60 with a magnet (not expressly shown) disposed on the end of connector 216, 216a or 216b.

For some applications exterior portion of connector 50 may include an enlarged tapered portion adjacent to first end 51. A plurality of longitudinal ridges 53 may also be formed on the exterior of connector 50 proximate first end 51. The enlarged tapered portion and/or longitudinal ridges 53 may allow an operator to grasp associated penetrator assembly 60 during attachment with a driver and may facilitate disengagement of connector 50 from hub 70 after outer penetrator or cannula 84 has been inserted into a bone and associated bone marrow.

Second opening 56 may be formed in second end 52 of connector 50. For example threads 57 may be formed on interior portions of opening 56 extending from second end 52. Threads 57 may be sized to engage threads 77 formed on an exterior portion of hub 70. Threads 57 and 77 may be characterized as forming portions of a Luer lock connection. However, the present disclosure is not limited to threads 57 and 77. Various types of releasable connections including, but not limited to, other types of Luer lock connections may be formed on adjacent portions of connector 50 and hub 70.

Trocar or inner penetrator 62 may be securely engaged with connector 50 extending from second end 52. The dimensions and configuration of inner penetrator 62 may be selected to allow inner penetrator 62 to be slidably inserted into longitudinal bore 83 of outer penetrator or cannula 80. Trocar 62 may include first end or tip 64. The dimensions and configuration of tip 64 may be selected to accommodate inserting penetrator assembly 60 into bone and associated bone marrow at a selected target area in a patient.

Hub 70 may include first end 71 and second end 72. First end 71 of hub 70 may have a generally cylindrical pin-type configuration compatible with releasably engaging hub 70 with second end or box end 52 of connector 50. As previously noted, threads 77 formed adjacent to end 71 of hub 70 may be releasably engaged with threads 57 formed on interior portions of opening 56 of connector 50.

For some applications second end 72 of hub 70 may have the general configuration of a flange. The dimensions and configuration of second end 72 of hub 70 may be varied to accommodate various insertion sites for an IO device. Hub 70 may be formed with a wide variety of flanges or other configurations compatible with contacting a patient's skin adjacent a desired insertion site.

Passageway 76 may extend from first end 71 through hub 70 to second end 72. Portions of passageway 76 extending from second end 72 may have dimensions selected to be compatible with securely engaging exterior portions of outer penetrator or cannula 80 with hub 70. Second end 82 of cannula 80 may be disposed within passageway 76 between first end 71 and second end 72. First end 81 of cannula 80 may extend from second end 72 of hub 70. Portions of passageway 76 extending from first end 71 of hub 70 may have an enlarged inside diameter to accommodate attachment with various types of fluid connectors. For example, see FIG. 9B.

Cannula or outer penetrator 80 may have longitudinal bore 83 extending from first end 81 to second end 82. Exterior dimensions of trocar or inner penetrator 62 are preferably selected to allow inner penetrator 62 be inserted through outer penetrator 80 with first end 64 of inner penetrator 62 generally aligned with first end 81 of outer penetrator 80 after threads 77 have been engaged with threads 57.

Tip 81 of outer penetrator 80 and/or tip 64 of inner penetrator 62 may be operable to penetrate bone and associated bone marrow. The configuration of tips 81 and 64 may be selected to penetrate a bone, bone marrow and other portions of a patient's body with minimum trauma. For some applications tip 64 of inner penetrator 62 may have a generally trapezoid shape with one or more cutting surfaces.

For some applications tips 81 and 64 may be ground together as a single unit during an associated manufacturing process. Providing a matching fit allows respective tips 81 and 64 to act as a single drilling unit to minimize damage as portions of penetrator assembly 60 are inserted into a bone and associated bone marrow.

Inner penetrator 62 may sometimes include a longitudinal groove (not expressly shown) that runs along one side of inner penetrator 62 to allow bone chips and/or tissue to exit an insertion site as penetrator assembly 60 is drilled deeper into an associated bone. Outer penetrator 80 and/or inner penetrator 62 may be formed from various materials including, but not limited to, stainless steel, titanium or any other material having suitable strength and durability to penetrate bone and associated bone marrow. The combination of hub 70 with cannula 80 may sometimes be referred to as an "intraosseous needle." The combination of trocar 62 with cannula 80 may sometimes be referred to as a "penetrator set" or an "IO needle set."

Hub 70 and particularly flange 72 may be used to stabilize intraosseous device 60 after insertion into a selected target area of a patient. Second end 52 of connector 50 may be releasably engaged from first end 71 of hub 70 after insertion of outer penetrator 80 into associated bone marrow. The depth of such insertion will be dependent upon the different distance between tip 81 of cannula 80 and flange 72 of hub 70. Various types of tubing may then be engaged with threads 77 formed on the exterior of hub 70 proximate first end or pin end 71.

Annular slot or groove 74 may be formed within second end 72 and sized to receive one end of protective cover or needle cap 94. Slot or groove 74 may be used to releasably engage cover 94 with penetrator assembly 60. For some applications cover 94 may be described as a generally hollow tube having rounded end or closed end 96. Cover 94 may be disposed within annular groove 74 to protect portions of outer penetrator 80 and inner penetrator 62 prior to attachment with a manual driver or a powered driver. Cover 94 may include a plurality of longitudinal ridges 98 formed on the exterior thereof. Longitudinal ridges 98 may cooperate with each other to allow installing and removing cover or needle cap 94 without contaminating portions of an associated penetrator needle or IO device. Cover 94 may be formed from various types of plastics and/or metals.

Figure 4:
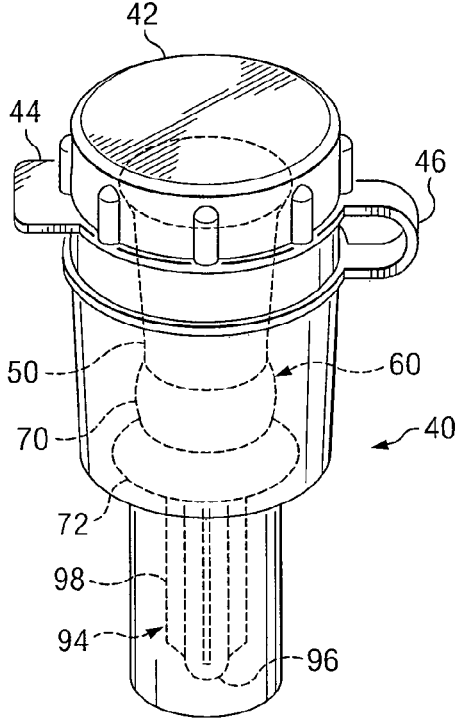
FIG. 4 is a schematic drawing showing an isometric view of an intraosseous device disposed in a container.

Container 40 as shown in FIG. 4 may include lid 42 along with tab 44. Tab 44 may be configured to allow lid 42 to be flipped open with one or more digits of an operator's hand. With lid 42 open, an operator may releasably engage a driver with an IO device disposed in container 40. For example, connector 216 of powered driver 200 may be releasably engaged with connector receptacle 54 of penetrator assembly 60. FIG. 2. Flexible connector 46 may be used to retain lid 42 with container 40 after lid 42 has been opened.

Various examples of supporting structures, supporting devices, attachment mechanisms and attachment techniques incorporating teachings of the present disclosure are shown in FIGS. 5-14. Various features of the present disclosure may be discussed with respect to bone 152 and associated bone marrow 154 as shown in FIGS. 5, 8, 9A-11 and 14. Bone 152 and bone marrow 154 may be representative of a portion of a patient's leg. Various examples of monitoring apparatus, equipment, devices, techniques and methods to evaluate performance of an intraosseous device are shown in FIGS. 9A, 9B and 10.

One example of an intraosseous device inserted into bone and associated bone marrow along with a supporting structure and attachment mechanism incorporating teachings of the present disclosure is shown in FIG. 5. For this example, the intraosseous device may be generally described as intraosseous (IO) needle 160 having a hollow, longitudinal bore extending therethrough (not expressly shown). First end or tip 161 of IO needle 160 may be designed to drill or cut through bone 152 and penetrate associated bone marrow 154. Tip 161 may be open to allow communication of fluids with bone marrow 154. Also, one or more side ports 164 may be formed in IO needle 160 to allow communication of fluids therethrough.

Second end 162 of IO needle 160 may have various types of connections including, but not limited to, a conventional Luer lock connection (not expressly shown) associated with supplying IV fluids and/or medications to a patient. For embodiments such as shown in FIGS. 5, 8, 9A and 10 connector receptacle 164 may be formed adjacent to second end 162. Connector receptacle 164 may have an enlarged outside diameter as compared with other portions of IO needle 160.

For some applications IO device 160 may have a tapered exterior to provide a better or tighter fluid seal with adjacent portions of bone 152 to prevent extravasation. Prior IO needles typically have a uniform outside diameter between fourteen (14) gauge (large) and eighteen (18) gauge (small). Increases in outside diameter or taper of IO device 160 may be selected to provide an enhanced fluid seal between exterior portions of IO device 160 and bone 152. The increases in the outside diameter or taper of IO device 160 may be limited to prevent fracture of bone 152 as IO device 160 is advanced into bone 152 and bone marrow 154. For some applications, IO device 160 may have a tapered outside diameter that increases by approximately one (1) gauge size. For example IO device 160 may have a sixteen (16) gauge diameter proximate first end 161 and a fifteen (15) gauge diameter proximate connector receptacle 164. However, other gauges and tapers may also be used.

The result of forming a good fluid seal between exterior portions of IO device 160 and adjacent portions bone 152 is that fluids and/or drugs injected through IO device 160 will flow into the patient's vascular system. The result of a broken fluid seal (or loose fluid seal) may be that some of the fluid will extravasate (leak) into surrounding tissues and may cause a compartment syndrome. This condition is a potentially serious complication associated with the use of IV and IO devices. Pressure from leaking fluid may build up in a limb or other portions of a patient's body which have only limited capacity for expansion. Problems resulting from excessive fluid pressure in tissue adjacent to an IV or IO insertion site will be discussed later.

Supporting structure 180 and attachment mechanism 170 such as shown in FIGS. 5 and 6 may be used with IO devices 60, 160 and 160a or any other type of IO device. Attachment mechanism 170 may be formed from various types of elastomeric and/or nonelastomeric materials compatible with contacting skin 156 and other soft tissue covering a patient's bone at a selected insertion sight or target area. The dimensions and configuration of attachment mechanism 170 may be selected to form satisfactory engagement with adjacent portions of leg 150, an arm, or other selected target site for providing access to a patient's vascular system.

For some applications attachment mechanism 170 may be generally described as a strap having first end 171 and second end 172 sized to be inserted through holes 181 and 182 of supporting structure 180. Strap 170 and supporting structure 180 cooperate with each other to prevent accidental removal or withdrawal of IO needle 160 from an insertion site. Strap 170 and supporting structure 180 also cooperate with each other to prevent excessive movement or rocking of IO device 160 relative to the insertion site.

Supporting structure 180 may include relatively short, hollow cylinder 184 with a pair of flaps, tabs or wings 186 extending therefrom. Holes 181 and 182 may be formed in respective tabs 186. Tabs 186 may be formed from relatively flexible material which will conform with adjacent portions of a patient's skin, soft tissue and bone. Hollow cylinder 184 may be formed from material with sufficient strength to prevent undesired movement of IO device 160. Interior dimensions of hollow cylinder 184 may correspond generally with exterior dimensions of IO needle 160 to provide a relatively snug fit therebetween.

For some applications attachment mechanism 170 may be used to releasably engage supporting structure 180 at a desired insertion site. An intraosseous device such as IO needle 160 may then be inserted through longitudinal bore 188 of supporting structure 180. For other applications IO needle 160 may first be inserted into bone marrow 154. Inside diameter 188 of cylinder 184 may be selected to be compatible with the dimensions and configuration of second end 162 such that supporting structure 180 may be inserted over or releasably engaged with IO needle 160 after insertion into bone marrow 154. For example, the dimensions of second end 162 may be substantially reduced as shown in FIG. 5. Alternatively, cylinder 184 may be formed from material having sufficient flexibility to accommodate expanding supporting structure 180 to fit over the exterior of IO device 160.

Figure 7:
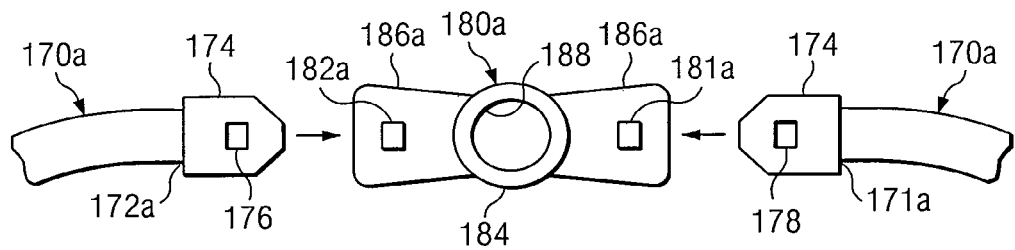
FIG. 7 is a schematic drawing showing a plan view with portions broken away of another example of an intraosseous device supporting structure and attachment mechanism incorporating teachings of the present disclosure.

For embodiments such as shown in FIG. 7, supporting structure 180a may include wings, tabs or flaps 186a which have been modified to include respective projections 181a and 182a extending therefrom. Strap 170a may be modified as compared with strap 170 by attaching respective buckles 174 with first end 171a and second end 172a. Each buckle 174 may include respective opening or hole 176 sized to receive associated projection 181a and 182a formed on tabs 186a.

Supporting structure 180a may be placed at an IO insertion site. Buckle 174a at first end 171a of strap 170a may be releasably engaged with corresponding projection 181a. Strap 170a may then be extended around patient's leg or other portions of a patient's body to allow engaging buckle 174a at second end 172a with associated projection 182a. For some applications, strap 170a may be formed from elastomeric material.

For some applications supporting structure 180a may be placed at an insertion site prior to installing IO device 160. IO device 160 may then be inserted through hollow cylinder 184 of supporting structure 180a. For other applications an IO device with exterior dimensions and exterior configuration compatible with interior dimensions of longitudinal bore 188 of supporting structure 180a may first be installed at a desired insertion site. Supporting structure 180a may then be fitted over the installed IO device (not expressly shown) by placing the IO device through hollow cylinder 184 of supporting structure 180a. Buckles 174 strap 170a may then be engaged with respective projections 181a and 182a.

Figure 8:
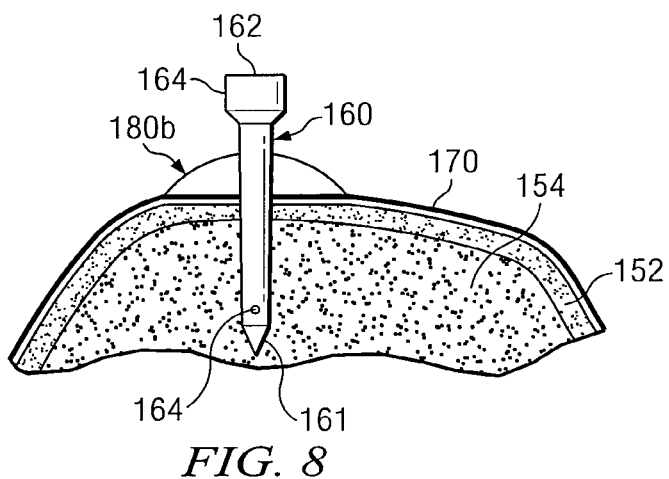
FIG. 8 is a schematic drawing in section and in elevation with portions broken away of an intraosseous device inserted into bone marrow of a patient along with another example of a supporting structure and attachment mechanism incorporating teachings of the present disclosure.

FIG. 8 shows IO needle 160 inserted into bone marrow 154. Supporting structure 180b may be used to stabilize IO needle 160 and limit excessive movement relative to bone 152. Supporting structure 180b may be generally described as having a domed shape configuration. The dimensions of supporting structure 180b may be selected to be compatible with a desired insertion site. A longitudinal bore or a longitudinal opening (not expressly shown) may extend through supporting structure 180b. The longitudinal bore may have dimensions compatible with exterior dimensions of IO needle 160.

Figure 12:
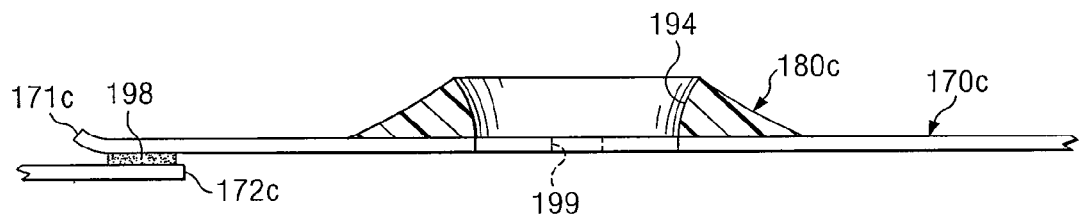
FIG. 12 is a schematic drawing in section with portions broken away of the supporting structure and attachment mechanism of FIG. 11.
Figure 14:
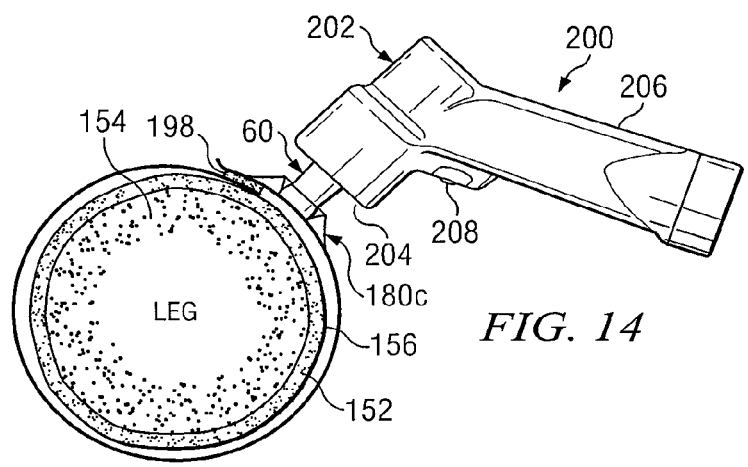
FIG. 14 is a schematic drawing in section showing an example of a powered driver and associated intraosseous device along with the supporting structure and attachment mechanism of FIGS. 11 and 12.

Supporting structure 180b may be formed from various types of semi-rigid silicone based materials and/or materials satisfactory for providing required support. A pair of holes (not expressly shown) may be provided in supporting structure 180b to accommodate the use of strap 170. However, other straps such as shown in FIGS. 11, 12 and 14 may be satisfactorily used to attach supporting structure 180 at a desired insertion site.

The muscles in a patient's limbs are typically split into respective enclosed spaces or "compartments" bound by strong and relatively unyielding membranes of fibrous tissues (deep fascia). Such enclosed spaces may also be referred to as "fascial compartments." Fibrous tissue or membranes effectively wrap around or surround respective muscle groups attached with the same bones. For example the lower leg of humans typically has four (4) compartments. Each compartment has a respective blood and nerve supply.

Compartment syndrome (sometimes referred to as "compartmental syndrome") may be generally described as a condition associated with increased pressure within an enclosed or limited space (compartment) of a patient's body that interferes with normal circulation of fluids (blood) and tissue functions within the compartment. Compartment syndrome is of particular concern with respect to a patient's limbs (legs, feet, arms and hands). Apparatus and methods of the present disclosure are not limited to monitoring a patient's limbs for compartment syndromes.

Compartment syndromes may be further characterized as acute, chronic, or secondary. Acute compartment syndromes are generally secondary to trauma and may have significantly elevated intracompartmental pressures. Acute compartment syndrome may occur when tissue pressure exceeds venous pressure and impairs blood flow out of the compartment. Sustained elevation of tissue pressure generally reduces capillary profusion below required levels for tissue viability and may irreversibly damage muscles and nerves within an affected compartment. Compartmental syndrome may occur when tissue pressure within a compartment exceeds associated profusion pressure.

Acute compartmental syndromes may occur following bone fractures, vascular damage, crushing of a limb or other body part and other injuries. Rapid onset and decreased circulation increases the need for prompt diagnosis and sometimes surgical decompression to avoid necrosis and long-term dysfunction. Untreated acute compartment syndromes may result in loss of limb functions and/or loss of a limb.

Leakage of fluids and/or drugs from a vein into surrounding tissue during an intravenous procedure or from a bone into surrounding tissue during an intraosseous procedure may also produce a compartment syndrome. Leakage of IV and IO fluids and drugs may be referred to "extravasation." Resulting injuries and/or damage associated with extravasation may be very serious.

Chronic compartment syndromes are generally milder, recurrent and often associated with exercise, repetitive training or physical exertion. Chronic compartment syndromes usually resolve with rest but may progress to an acute form if associated physical activity is continued Supplying fluid to bone marrow using an intraosseous device may result in increased pressure in an adjacent compartment if fluid integrity of an associate bone containing the bone marrow has been compromised. For example a vehicle accident may result in a bone fracture allowing fluid communication with an adjacent compartment. Various diseases or chronic conditions may result in deterioration of a bone and allow fluid communication between associated bone marrow and an adjacent compartment. Monitoring a patient's extremity (limb) for such pressure increases may be appropriate if damage or injury has occurred to the extremity (limb). An intraosseous injection site other than a damaged limb or extremity should generally be selected whenever possible.

Extravasation and potentially resulting compartment syndrome may be an undesired side effect of administration of fluids via intraosseous device. Extravasation may occur if there has been damage and/or deterioration of the associated bone. Extravasation may also occur if there is not a satisfactory fluid seal between exterior portions of an IO device and adjacent portions of an associated bone. The use of monitors, pressure sensors or strain gauges and other apparatus in accordance with teachings of the present disclosure may provide an early warning or early notice of possible pressure increases which may lead to undesired side effects such as compartment syndromes if not corrected.

Apparatus and methods to detect extravasation and potential compartment syndrome may be incorporated into supporting structures and/or attachment mechanism for an IO device in accordance with teachings of the present disclosure. For example, a strap may be equipped with a stain gauge or pressure sensor to detect an increase in size of a limb indicating a possible impending compartment syndrome.

Figure 9A:
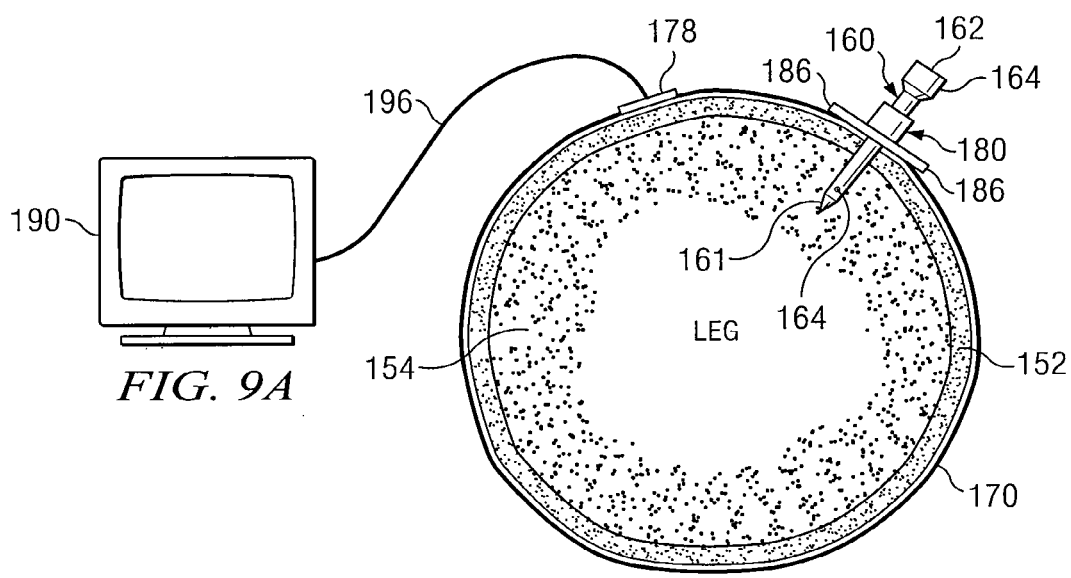
FIG. 9A is a schematic drawing in section with portions broken away showing an intraosseous device inserted into bone marrow of a patient along with another example of a supporting structure, attachment mechanism and monitoring apparatus incorporating teachings of the present disclosure.

FIG. 9A shows IO device 160 seated in bone 152 and associated bone marrow 154. Strap 170 may be placed around bone 152 and attached to supporting structure 180 as previously described. Sensor 178 may be attached to strap 170 for use in measuring various parameters associated with providing fluids and/or medications through IO device 160 to bone marrow 154. Such parameters may include, but are not limited to, pressure and/or changes in the size of a patient's limb, temperature and/or pulse rate. For example, sensor 178 may be a strain gauge operable to measure and detect increased stress placed on strap 170 by swelling, expansion or change size of a patient's limb.

For some applications sensor 178 may be coupled with monitor and/or general purpose computer 190 via signal wire 196. When monitor 190 detects a preset value for one or more of these parameters, an alarm may be sounded. Monitor 190 may also include one or more programs operable to stop infusion of fluids and/or medication through IO device 160 in the event one or more parameters exceeds a preset limit.

Another method of detecting a potential compartment syndrome may include directly inserted sensor into a compartment and connecting a pressure sensor with an appropriate pressure monitor. For some applications tubing may be used to connect a hollow needle with a pressure sensor. The pressure sensor may be connected with a pressure monitor. For some applications the hollow needle, tubing and pressure sensor may contain a saline solution. An increase in pressure within the compartment may be used to alert medical personnel that a serious condition may be developing.

For embodiments such as shown in FIG. 9B cannula 80 of intraosseous device 60 may be inserted into the tibia of leg 150. Various types of IO and IV fluid connectors may be releasably engaged with first end 71 of hub 70. For embodiments such as shown in 9B, right angle connector 130 may include Luer lock fitting 132 operable to be releasably engaged with first end 71 of hub 70. Right angle connector 130 may be satisfactorily used to couple IO device 60 with various sources of medication and/or fluids. For example, IV bag 140 may be connected with right angle connector 130 using flexible tubing 142 and tubing connectors 144. Various types of control valves and/or outlet mechanisms 146 may be used to regulate the flow of fluid from IV bag 140 through tubing 142, right angle connector 130 to intraosseous device 60. For some applications control valve 146 may include an electrical actuator (not expressly shown).

For embodiments such as shown in FIG. 9B one or more sensors may be placed in a compartment of a patient's limb or extremity adjacent to an intraosseous insertion site. Such sensors may be used to detect pressure, temperature, oxygen levels, carbon dioxide levels, lactic acid concentrations and/or concentration of drugs, medications or chemicals contained in the IV or IO fluids communicated through IO device 60. For example, pressure sensor 100 may be inserted into a compartment of leg 150 containing an associated calf muscle to detect any increased pressure in the compartment. Such pressure increase may result from communication or extravasation of fluid between the bone marrow and the calf muscle or compartment via damaged or deteriorated portions of bone 152.

Monitor 190 may be used to alert medical personnel that the pressure is increasing and that a serious condition such as a compartment syndrome may develop. Monitor 190 may also alert medical personnel concerning temperature changes, undesired oxygen or carbon dioxide levels or the presence of any drugs, medication or chemical associated with IV or IO fluids communicated through IO device 60.

Various types of control mechanisms, general purpose computers and/or monitors 110 may be engaged with sensor 100. For some applications an electrical cable or conductor 102 may be engaged with sensor 100. For other applications (not expressly shown) sensor 100 may be a generally hollow needle. A hollow tube may connect sensor 100 with a pressure monitor.

For some applications an electrical cable or wire 112 may be connected between pressure monitor 110 and control valve 144. When monitor 110 receives a pressure which exceeds a preselected value, control valve 146 may be activated to block or prevent further flow of fluid from IV bag 140 to intraosseous device 60.

FIG. 10 shows IO device 160*a* inserted into bone 152 and associated bone marrow 154. IO device 160*a* may be equipped with pressure transducer 192 proximate tip 161 to measure intraosseous pressure. For some applications, a similar needle may be placed in a leg muscle to measure intra-compartment pressure. See FIG. 9B.

Seal assembly 195 may be used to isolate signal wire 196 so that infusions of fluids may proceed while, at the same time, measuring intravenous pressure at tip 161. Various types of elastomeric materials may be used to form seal assembly 195. For some applications one or more valves (not expressly shown) may also be used to isolate signal wire 196 from fluid flowing through IO device 160*a*.

Measurements from sensor 192 may be analyzed by a computer (not expressly shown) to manage changes in a patient's condition by initiating pre-set changes in infusion pressure, controlling the rate of infusion or stopping infusion all together and alerting the patient and/or medical personnel if pressure limits are exceeded.

Figure 13:
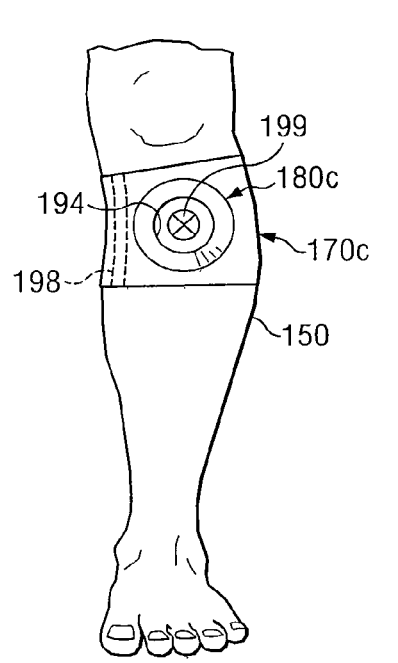
FIG. 13 is a schematic drawing showing an isometric view with portions broken away of the supporting structure and attachment mechanism of FIGS. 11 and 12 releasably attached to a patient proximate the tibia.

FIGS. 11, 12 and 13 show one example of a supporting structure or guide which may be disposed at a desired insertion site such as the upper tibia proximate a patient's knee. Supporting structure or guide 180*c* may be generally described as having a dome shaped configuration with cavity or opening 194 formed therein and sized to receive an intraosseous device. For example, opening 194 may be sized to accommodate an intraosseous device such as penetrator assembly 60. See for example FIG. 3.

Supporting structure or guide 180*c* may be formed from various polymeric and/or thermoplastic materials having desired rigidity and strength to direct insertion of an intraosseous device at a desired insertion site. Supporting structure 180*c* may also be formed from various types of elastomeric and/or nonelastomeric materials satisfactory for use in forming a guide or supporting structure to direct insertion of an intraosseous device at a desired insertion site and/or to stabilize an IO device at an insertion site.

For some applications strap 170*c* may include one or more strips of hook and loop type material 198 (sometimes referred to as Velcro® strips) disposed proximate first end 171*c* and second end 172*c* of strap 170*c*. The configuration, size and dimensions of Velcro® strips 198 may be modified to allow strap 170*c* to releasably attach supporting structure 180*c* with a leg or other portions of a patient's body having various dimensions. For some applications supporting structure 180*c* may include target 199 disposed within opening 194 for use by an operator to more precisely direct installation of an associated IO device at a desired insertion site.

FIG. 14 shows powered driver 200 being used to insert penetrator assembly 60 at an insertion site identified by guide or supporting structure 180*c*. For some applications interior portions of opening 194 may have a generally convex configuration compatible with guiding and supporting adjacent portions of penetrator assembly 60. Powered driver 200 may be further stabilized with various types of straps and/or medical grade tape (not expressly shown) prior to inserting penetrator assembly 60.

Extravasation (leakage) of cytotoxic drugs into subcutaneous tissues adjacent to an insertion site during cancer treatment may be devastating. To prevent extravasation (leakage) of cytotoxic drugs or other fluids, an IO device incorporating teachings of the present disclosure may include a tapered exterior with progressively larger outside diameters to form a satisfactory fluid seal with adjacent bone. A wide variety of medically approved adhesives and sealants may also be disposed on exterior portions of an IO device to provide a satisfactory fluid seal. Methylene blue dye may be injected into an IO device to detect any fluid leak between exterior portions of the IO device and adjacent bone.

Figures 15A, 15B:
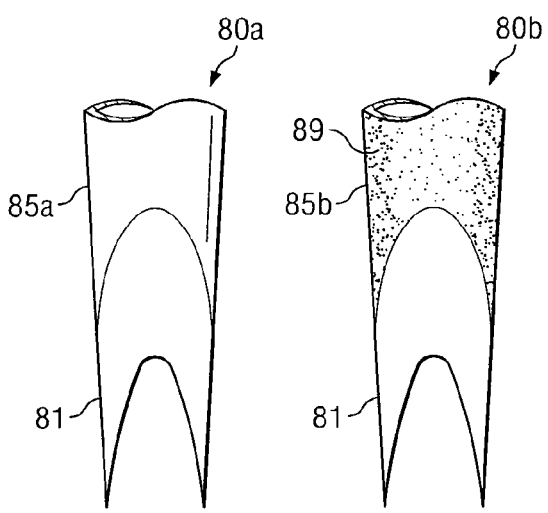
FIG. 15A is a schematic drawing in section with portions broken away showing another example of an intraosseous device incorporating with teachings of the present disclosure.
FIG. 15B is a schematic drawing in section with portions broken away showing another example of an intraosseous device incorporating with teachings of the present disclosure.

For embodiments such as shown in FIG. 15A, IO device 80*a* may include tapered exterior 85*a* which provides a better or tighter fluid seal with adjacent portions of a bone at an insertion site to prevent extravasation. Increases in the outside diameter of IO device 80*a* may be limited to prevent fracture of a bone at an insertion site as IO device 80*a* is advanced into the bone and associated bone marrow. The increase in outside diameter 85*a* of IO device 80*a* may be selected to provide an enhanced fluid seal between tapered exterior 85*c* and adjacent portions of the bone.

IO needles are typically described as having a gauge size corresponding with the diameter. IO needles typically range with gauges between the range of eighteen (18) to fourteen (14). A fourteen gauge IO need is larger than eighteen gauge. For some applications, IO devices 80*a* and 80*b* may generally be described as an IO needle having a tapered outside diameter that increases from approximately one gauge size such as from sixteen (16) gauge adjacent first end 81 to approximately fifteen (15) gauge adjacent an associated hub.

For embodiments such as shown in FIG. 15B, IO device 80*b* may include tapered exterior surface 85*b* with sealant layer 89 disposed thereon. A wide variety of medical grade sealants and adhesives may be satisfactorily disposed on exterior portions of IO device 80*b* including, but not limited to, silicone and methyl methacrylate. Tapered exterior 85*b* and sealant layer 89 may cooperate with each other to provide an enhanced or tighter fluid seal between adjacent portions of a bone at an insertion site to prevent extravasation. The increase in outside diameter of IO device 80*b* may be limited as previously described with respect to IO device 80*b*.

Sealant layer 89 may also be disposed on exterior portions of IO device 80, 80*a*, 160 and 160*a* or any other IO device incorporating teachings of the present disclosure to substantially minimize or prevent extravasation The use of medical grade sealants and adhesives is not limited to IO devices having tapered, exterior surfaces.

The result of forming a satisfactory fluid seal between exterior portions of an IO device and adjacent portions a bone is that fluids and/or drugs injected through such IO devices will not leak into adjacent tissue. The result of a broken fluid seal (or loose fluid seal) may be that some of the fluid will extravasate (leak) into surrounding body tissues and may cause serious damage. IO devices 80, 80*a*, 80*b*, 160 and/or 160*a* and any other IO device incorporating teachings of the present disclosure may also have an interior coating of Heparin or other anticoagulants to prevent clotting. An exterior coating of a suitable antibiotic to prevent infection may also be used with an IO device incorporating teachings of the present disclosure.

Examples of acute and chronic conditions which may be treated using intraosseous devices, intravenous devices and procedures incorporating teachings of the present disclosure include, but are not limited to, the following:

Anaphylaxis (epinephrine, steroids, antihistamines, fluids, and life support);

Arrhythmia (anti-arrhythmics, electrolyte balance, life support);

Burns (fluid replacement, antibiotics, morphine for pain control);

Cardiac arrest (epinephrine, atropine, amiodarone, calcium, xylocaine, magnesium);

Congestive heart failure (life support, diuretics, morphine, nitroglycerin);

Dehydration (emergency port for life support, antibiotics, blood, electrolytes);

Diabetic Ketoacidosis (life support, electrolyte control, fluid replacement);

Dialysis (emergency port for life support, antibiotics, blood, electrolytes);

Drug overdose (naloxone, life support, electrolyte correction);

Emphysema (life support, beta adrenergics, steroids);

Hemophiliacs (life support, blood, fibrin products, analgesics);

Osteomyelitis (antibiotics directly into the site of infection, analgesics);

Pediatric applications (shock, dehydration, nutrition, electrolyte correction);

Seizures (anti-seizure medications, life support, fluid balance);

Shock (life support fluids, pressor agents, antibiotics, steroids);

Sickle cell crisis (fluid, morphine for pain, blood, antibiotics); and

Trauma (emergency port for life support fluids, antibiotics, blood, electrolytes).

More than 35,000 Advanced Cardiac Life Support (ACLS) ambulances are in service in the U.S. Each is equipped with emergency drugs and devices. Most are required to carry intraosseous needles and paramedics are trained in their use for pediatric emergencies. Kits incorporating teachings of the present disclosure may be used to administer medications and treats before permanent damage to a patient occurs.

More than 4,000 emergency rooms in the U.S. are required to treat life-threatening emergencies like shock trauma and cardiac arrest. ERs are stocked with the latest devices and equipment to help patients receive state-of-the-art treatment. However, there is no more exasperating situation for the physician or potentially catastrophic condition for the critical patient, than the inability to establish intravenous access. Kits with IO devices incorporating teachings of the present disclosure may provide a simple and straightforward solution for extremely difficult clinical problems.

Hospitals are required to provide crash carts on every patient ward. It is estimated that 6,000 U.S. hospitals stock more than 60,000 crash carts. These crash carts are stocked with defibrillators, IV access devices, including central venous catheters, IV fluids and drugs for common emergencies. Nurses and other healthcare workers using these crash carts are often inexperienced in such emergencies and have difficulty establishing IV access. A kit with IO devices incorporating teachings of the present disclosure may provide the long sought IV alternative for difficult patients.

Automatic injectors are widely used in the military. During Desert Storm, combat soldiers carried an atropine auto-injector for nerve gas poisoning. Current auto-injectors are limited to intramuscular injections. The Kits with IO devices may vastly expand the scope of treatment to include intravenous drugs, without having to be skilled in the technique of intravenous insertion.

Most acute care hospitals in the U.S. operate Intensive Care Units (ICUs) for seriously ill patients. Establishing and maintaining venous access in these patients is often a challenge. IO access may be a welcome procedure for administration of drugs and fluids to these critical patients.

Ten percent of the population experience a major seizure in their lifetime and more than 2,500,000 people in the United States have epilepsy. Grand mal seizures represent one of the most dramatic events in medicine. During the seizure, which usually lasts 60 to 90 seconds, patients typically fall to the ground, become rigid with trunk and extremities extended, and shake violently. The most dreaded progression of seizures is status epilepticus, a condition defined as a continuous seizure lasting more than 30 minutes or two or more seizures that occur without full conscious recovery between attacks. Convulsive status epilepticus requires urgent, immediate treatment. Patients are at risk for serious injury, hypoxemia, circulatory collapse, permanent brain damage and death. The overall mortality of convulsive status epilepticus is up to approximately thirty-five percent (35%).

Intravenous access with a large bore needle/catheter must be established to administer anticonvulsant medications. These include a benzodiazepine followed by phenytoin and/or phenobarbitol for immediate seizure control and prevention of further seizures. There are no satisfactory oral, rectal, or intramuscular medications that will control status epilepticus.

The problem facing clinicians and paramedics treating patients with status epilepticus is the difficulty establishing venous access. Without adequate venous lines none of the effective anticonvulsants can be given. During seizures the violent shaking makes accessing a satisfactory vein difficult. Often after the line is established, further shaking dislodges the IV or causes it to infiltrate.

Further, caregivers are at great risk of puncturing themselves with a needle when attempting to establish venous access in a patient during a seizure. Through no fault of their own, seizing patients, by jerking and thrashing around, turn the safest procedure into a terrifying venture. Doctors, nurses, and paramedics work in mortal fear of contracting AIDS and hepatitis through an inadvertent puncture with a contaminated needle.

In an attempt to solve the venous access problem, emergency physicians and intensivists have turned to establishing a central line (intravenous catheter placed in a large central vein such as the subclavian or femoral vein). However, with this method, even under ideal conditions, there is an increased incidence of serious side effects such as pneumothorax, hemothorax, inadvertent puncture of a major artery, infection, venous thrombosis, and embolus. In the case of a patient with status epilepticus, this method becomes increasingly difficult and dangerous for all of the above-mentioned reasons. Therefore, most doctors are reluctant to even attempt a central line until seizures have ceased.

Dialysis patients who often come to the emergency room in life threatening situations such as pulmonary edema (water on the lungs) or high potassium leading to cardiac arrest. These patients typically have troublesome or nonexistent veins. The IO access may give these patients hope for a better quality of live and decrease their mortality.

Drug overdose victims, often comatose, generally require immediate IV access to give antidotes and life saving medications such as Narcan. These patients usually have difficult venous access due to long term abuse of their veins. IO access may give these patients an alternate route for delivery of medications and fluids while improving the safety of the healthcare workers.

Trauma victims and attempted suicide patients, often in shock due to blood loss, may also require swift replacement of fluids to save vital organs. Because of the shock condition (decreased blood pressure), veins collapse and are often impossible to find. IO access may save precious minutes for paramedics and trauma surgeons responsible for their care.

Although the present disclosure and its advantages have been described in detail, it should be understood that various changes, substitutions and alternations can be made herein without departing from the spirit and scope of the disclosure as defined by the following claims.

What is claimed is:

1. A system for monitoring performance of an intraosseous device disposed in bone marrow in a patient's limb comprising:
   an intraosseous first device having a first end operable to be disposed into a first insertion site and within bone marrow of a bone and a second end operable to be connected with tubing;
   the tubing operable to communicate fluid between a fluid source and the bone marrow;
   a second device operable to be disposed into a second insertion site and into a compartment of a patient's limb adjacent to the bone, the second device including a pressure sensor operable to monitor pressure in the compartment; and
   the pressure sensor operable to detect any increase in the pressure within the compartment.

2. The system of claim 1 further comprising:
   the fluid source having a control valve; and
   the pressure sensor operable to close the control valve when the pressure in the compartment reaches a preset level.

3. The system of claim 1 further comprising:
   a hollow needle configured for insertion into the compartment;
   a hollow tube connecting the hollow needle with the pressure sensor; and
   the pressure sensor connected to a pressure monitor.

4. The system of claim 1 further comprising:
   an alarm configured to provide an alert,
   the pressure sensor operable to activate the alarm to provide the alert when the pressure in the compartment reaches a preset level.

5. The system of claim 3 wherein the hollow needle, the hollow tube, and the pressure sensor are configured to contain an ionic solution.

* * * * *